US012778438B2

(12) United States Patent
Zhang

(10) Patent No.: US 12,778,438 B2
(45) Date of Patent: Nov. 3, 2026

(54) SYSTEMS, APPARATUS, AND METHODS FOR MEASURING HEART RATE

(71) Applicant: Intel Corporation, Santa Clara, CA (US)

(72) Inventor: Guoqing Zhang, Tampere (FI)

(73) Assignee: Intel Products IP LLC, Santa Clara, CA (US)

( * ) Notice: Subject to any disclaimer, the term of this patent is extended or adjusted under 35 U.S.C. 154(b) by 769 days.

(21) Appl. No.: 17/957,673

(22) Filed: Sep. 30, 2022

(65) Prior Publication Data

US 2023/0023965 A1 Jan. 26, 2023

(51) Int. Cl.

*A61B 5/024* (2006.01)
*A61B 5/00* (2006.01)
*A61B 5/0205* (2006.01)
*A61B 5/0507* (2021.01)

(52) U.S. Cl.

CPC ........ *A61B 5/02444* (2013.01); *A61B 5/0205* (2013.01); *A61B 5/0507* (2013.01); *A61B 5/7257* (2013.01)

(58) Field of Classification Search

None
See application file for complete search history.

(56) References Cited

U.S. PATENT DOCUMENTS

2021/0361172 A1* 11/2021 Fornell ................ A61G 7/0527
2022/0313112 A1* 10/2022 Wolfe .................. A61B 5/4806

OTHER PUBLICATIONS

Kazemi et al., “Cyclostationary Approach to Doppler Radar Heart and Respiration Rates Monitoring with Body Motion Cancelation Using Radar Doppler System,” Biomedical Signal Processing and Control 13 (2014), pp. 79-88, available online Apr. 25, 2014, 10 pages.

Mostafanezhad et al., “Application of Empirical Mode Decomposition in Removing Fidgeting Interference in Doppler Radar Life Signs Monitoring Devices,” 31st Annual International Conference of the IEEE EMBS, Sep. 2-6, 2009, pp. 340-343, 4 pages.

Wang et al., “mmHRV: Contactless Heart Rate Variability Monitoring Using Millimeter-Wave Radio,” IEEE Internet of Things Journal, vol. 8, No. 22, Nov. 15, 2021, pp. 16623-16636, 14 pages.

(Continued)

*Primary Examiner* — Jay B Shah
(74) *Attorney, Agent, or Firm* — Hanley, Flight & Zimmerman, LLC

(57) ABSTRACT

Systems, apparatus, and methods for measuring heart rate are disclosed. An example system includes a transmitter to emit electromagnetic waves; a first sensor to output signals representative of the electromagnetic waves reflected by a subject; a second sensor to generate image data, the image data including data corresponding to a chest of the subject; machine readable instructions; and processor circuitry to at least one of instantiate or execute the machine readable instructions to generate heartbeat data by cancelling harmonics associated with respiration by the subject from data corresponding to the output signals of the first sensor based on the image data, and determine a heart rate for the subject based on the heartbeat data.

20 Claims, 13 Drawing Sheets

(56) References Cited

OTHER PUBLICATIONS

Tu et al., "Respiration Harmonics Cancellation for Accurate Heart Rate Measurement in Non-contact Vital Sign Detection," available on IEEE Xplore on Jan. 2, 2014, https://ieeexplore.ieee.org/document/6697732, 3 pages.
Yu et al., "Doppler Radar Vital Signs Detection Method Based on Higher Order Cyclostationary," Sensors, vol. 18, published Dec. 26, 2017, 20 pages.
Hu et al., "A novel adaptive range-bin selection method for remote heart-rate measurement of an indoor moving person using mm-wave FMCW radar," ComEX, IEICE Communications Express, vol. 1, pp. 1-6, publicized Mar. 1, 2021, 6 pages.
Joshi, "Non-Contact Vital Sign Detection Using mm-Wave Radar," Masters Theses, TRACE: Tennessee Research and Creative Exchange, University of Tennessee, Knoxville, May 2022, 99 pages.
Iyer et al., "mm-Wave Radar-Based Vital Signs Monitoring and Arrhythmia Detection Using Machine Learning," Sensors, vol. 22. published Apr. 19, 2022, 20 pages.
Subramani, "Using mmWave radar for vital signs monitoring," Embedded.com, Aug. 17, 2020, retrieved from https://www.embedded.com/using-mmwave-radar-for-vital-signs-monitoring on Sep. 15, 2022, 12 pages.

* cited by examiner

SYSTEMS, APPARATUS, AND METHODS FOR MEASURING HEART RATE

FIELD OF THE DISCLOSURE

This disclosure relates generally to physiological signal analysis and, more particularly, to systems, apparatus, and methods for measuring heart rate.

BACKGROUND

A millimeter-wave (mmWave) radar sensor transmits pulses of electromagnetic waves to a target and detects signals reflected by the target via an antenna. Millimeter-wave radar can be used to measure heart rate of a human subject (e.g., a number of heartbeats within a time period, such as per minute).

BRIEF DESCRIPTION OF THE DRAWINGS

In general, the same reference numbers will be used throughout the drawing(s) and accompanying written description to refer to the same or like parts. The figures are not to scale.

Figure 1:
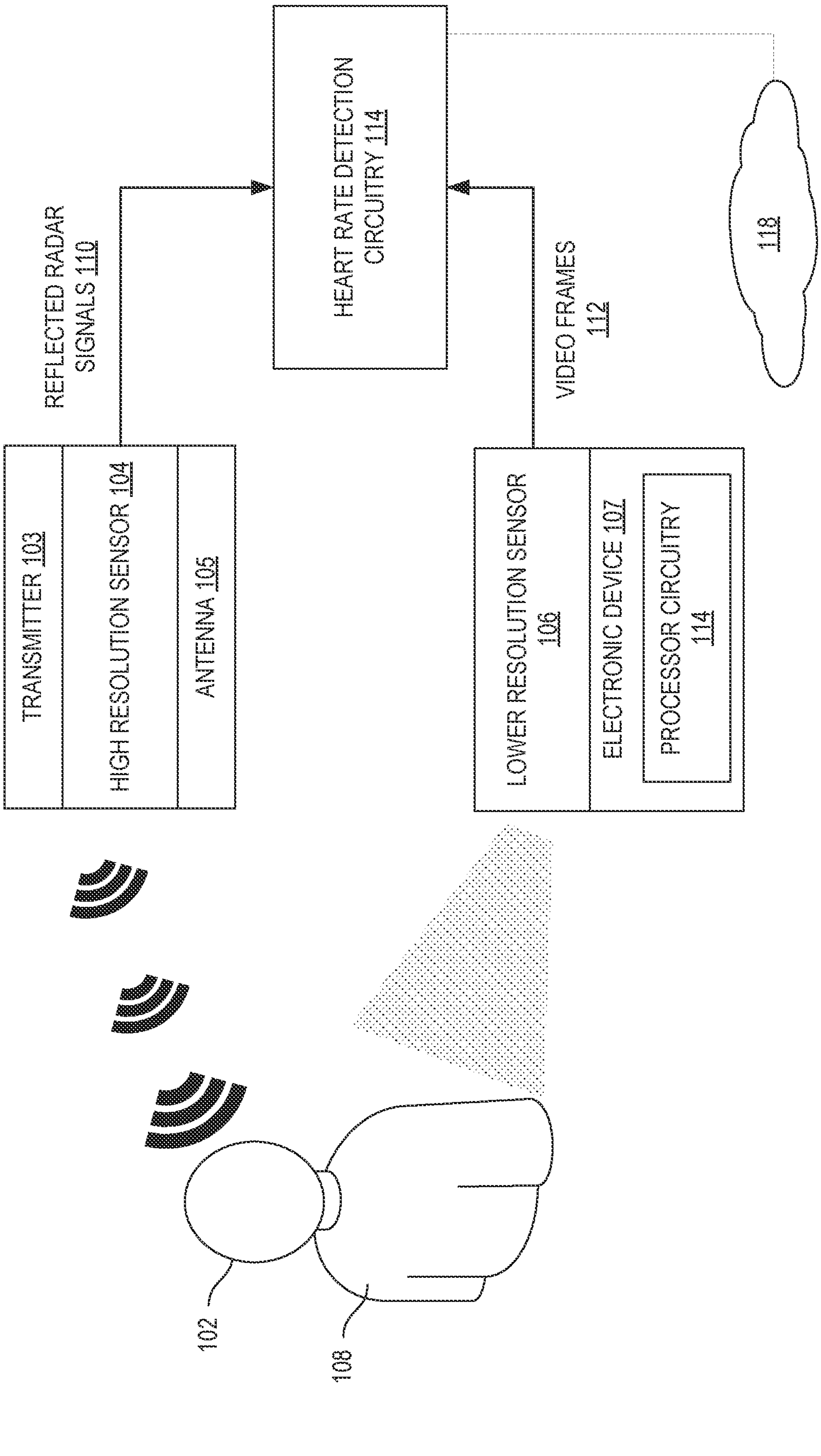
FIG. 1 illustrates an example system for measuring heart rate of a subject in accordance with teachings of this disclosure.

Unless specifically stated otherwise, descriptors such as "first," "second," "third," etc., are used herein without imputing or otherwise indicating any meaning of priority, physical order, arrangement in a list, and/or ordering in any way, but are merely used as labels and/or arbitrary names to distinguish elements for ease of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for identifying those elements distinctly that might, for example, otherwise share a same name.

As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

As used herein, "processor circuitry" is defined to include (i) one or more special purpose electrical circuits structured to perform specific operation(s) and including one or more semiconductor-based logic devices (e.g., electrical hardware implemented by one or more transistors), and/or (ii) one or more general purpose semiconductor-based electrical circuits programmable with instructions to perform specific operations and including one or more semiconductor-based logic devices (e.g., electrical hardware implemented by one or more transistors). Examples of processor circuitry include programmable microprocessors, Field Programmable Gate Arrays (FPGAs) that may instantiate instructions, Central Processor Units (CPUs), Graphics Processor Units (GPUs), Digital Signal Processors (DSPs), XPUs, or microcontrollers and integrated circuits such as Application Specific Integrated Circuits (ASICs). For example, an XPU may be implemented by a heterogeneous computing system including multiple types of processor circuitry (e.g., one or more FPGAs, one or more CPUs, one or more GPUs, one or more DSPs, etc., and/or a combination thereof) and application programming interface(s) (API(s)) that may assign computing task(s) to whichever one(s) of the multiple types of processor circuitry is/are best suited to execute the computing task(s).

DETAILED DESCRIPTION

Millimeter-wave (mmWave) radar can serve as a contactless manner for measuring heart rate of a human subject as compared to methods that involve physical contact with the subject (e.g., a heart rate monitor worn by the subject). For instance, a mmWave radar sensor can emit pulses of electromagnetic waves that are directed toward a chest of a subject who is in a stationary or substantially stationary position (e.g., sitting in a chair). The sensor can detect signals reflected by the chest of the subject via an antenna.

The reflected radar signals are modulated by displacement of the chest of the subject. Chest displacement is due to a combination of variables including movement of the subject's torso (e.g., due to fidgeting by the subject during the data collection), respiration, and heartbeat. However, the amount of the chest displacement due to the subject's heartbeat (e.g., 0.1-0.5 mm) is typically smaller than the displacement due to torso movement and respiration. Moreover, signal processing techniques such as Fast Fourier Transform may not adequately account for the effects of respiration in the resulting signal data. For instance, a respiration signal can be quasi-periodic (e.g., irregular) and include harmonic components (e.g., high order harmonic components) that appear in the frequency band of the heartbeat (e.g., 0.8-2.5 Hz). Thus, distinguishing between heartbeat and respiration in the reflected mmWave signals can be difficult.

Some known approaches that use mmWave radar to measure heart rate attempt to resolve the interference of higher order harmonics due to respiration by making assumptions about the periodicity of respiratory patterns.

For instance, some known methods assume that both respiration and heartbeat are periodic. Some known methods decompose the reflected radar signals into band-separated modes using techniques such as Empirical Mode Decomposition or Variational Mode Decomposition, where the radar signal is decomposed into band-separated modes and each mode has a central or carrier frequency and sideband frequencies higher or lower than the carrier frequency. In such instances, the signal components corresponding to respiration and the signal components corresponding to heartbeat are constrained to a mode in an effort to distinguish between respiration and heartbeat. However, both the periodicity assumptions and the mode-constrained assumptions with respect to respiration can introduce inaccuracies into the data analysis. For instance, a respiratory pattern of a user could be non-periodic or irregular due to, for instance, the subject taking a deep breath or holding his or her breath during data collection. Thus, the accuracy of the heart rate measurement in some known methods depends on respiratory pattern of the subject. Some known methods perform harmonic cancellation to reduce interference from respiration harmonics but may risk eliminating the heart rate signal if the heart rate signal happens to be within the frequencies of the respiratory harmonics.

Disclosed herein are example systems, apparatus, and methods to remove effects of harmonics due to respiration from signal data collected to measure heart rate of a subject. Examples disclosed herein use a contactless, heterogeneous-sensing system to measure heart rate, where the system includes (a) high resolution sensor(s) such as a radar (e.g., mmWave radar) sensor, a high resolution camera, a LIDAR sensor, and/or other type(s) of sensor(s) that provide for at least millimeter measuring accuracy, and (b) sensor(s) having a lower resolution than the high resolution sensor(s), such as webcam. Examples disclosed herein use data corresponding to the output(s) of the sensor(s) having the lower resolution to identify and track displacement of a portion of the chest of the subject due to respiration over time. For instance, the portion of the chest can be represented by pixel(s) having particular coordinates in a first frame of image data generated by the lower resolution sensor. As a result of chest displacement during respiration, the coordinates of the pixel(s) can change in subsequently generated image data.

Examples disclosed herein use the changes in location(s) of the chest point(s) (e.g., chest point pixel(s)) over time to remove signal artifacts due to respiration in the data corresponding to the signals output by the high resolution sensor(s). For instance, examples disclosed herein perform Short Time Fourier Transforms (STFT) for the data corresponding to the signals associated with the high resolution sensor(s) and the signals representing changes in the coordinates of the chest point pixel(s) over time. Examples disclosed herein subtract the STFT spectrum associated with the chest point pixel coordinate data from the STFT spectrum for the data corresponding to the high resolution sensor signals (e.g., radar echo signals) to cancel harmonics associated with respiration from the high resolution sensor signals. Put another way, examples disclosed herein separate respiration signal data from heartbeat signal data based on resolution differences between the high and low resolution sensors. The resulting data represents heart rate more accurately as compared to signal processing techniques that rely on assumptions such as periodicity of respiration. In particular, data that may mistakenly be classified as heartbeat data but is actually associated with respiration is removed. Thus, examples disclosed herein provide for contactless measurements of heart rate that remove signal artifacts due to respiration using resolution differences between two or more sensors.

Although examples disclosed herein are discussed in connection with heart rate measurements, examples disclosed herein could be used to perform harmonic cancellation for signal data in connection with other fields that use radio signal processing.

FIG. 1 illustrates an example system 100 for measuring heart rate of a subject 102 (e.g., a human). The example system 100 includes a high resolution sensor 104. The high resolution sensor 104 can include mmWave radar sensor(s), a high resolution camera, LIDAR sensor(s), and/or other sensor(s) that provide for measuring accuracy in at least the millimeter range (in view of the displacement range of the chest due to heartbeat (e.g., 0.1 mm-0.5 mm). For illustrative purposes, the example high resolution sensor 104 of FIG. 1 is a mmWave sensor. A transmitter 103 emits electromagnetic waves. An antenna 105 detects radar signals reflected by object(s) (e.g., the subject 102, inanimate objects in the environment in which the subject 102 is located such as furniture). In some examples, the antenna 105 includes a MIMO (multiple input, multiple output) antenna such that the antenna 105 includes multiple receiving channels. In some examples, the transmitter 103 and the high resolution sensor 104 are implemented by a transceiver.

The example system 100 includes a sensor 106 having a lower resolution than the resolution of the high resolution sensor 104. The lower resolution sensor 106 (e.g., one or more lower resolution sensors) can include, for instance, a camera such as a webcam of an electronic device 107 (e.g., a personal computing device such as a laptop). The lower resolution sensor 106 can include an ultrasonic sensor. For illustrative purposes, the example lower resolution sensor 106 of FIG. 1 is a webcam of the electronic device 107. In some examples, the higher resolution sensor 104 and the lower resolution sensor 106 are physically coupled via a rigid or substantially rigid connection. The rigid or substantially rigid coupling between the sensors 104, 106 can facilitate fusion of the data corresponding to the signals output by each sensor 104, 106 by enabling the data associated with each sensor 104, 106 to be transformed into a common coordinate system.

To measure the heart rate of the subject 102, the subject 102 may remain stationary or substantially stationary for a period of time (e.g., the subject sits in a chair for 60 seconds). The transmitter 103 associated with the high resolution sensor 104 (e.g., the mmWave radar sensor) emits electromagnetic wave pulses (e.g., via the antenna 105) that are directed to a chest 108 of the subject 102. The antenna 105 receives signals 110 representing the radar waves that are reflected by the subject's chest 108. Simultaneously or substantially simultaneously, the lower resolution sensor 106 (e.g., the webcam) collects data from (e.g., scans) the subject 102. In the example of FIG. 1, the outputs of the lower resolution sensor 106 include video frames 112 including images of the chest 108 of the subject 102. The lower resolution sensor 106 can generate the video frames 112 at a rate of, for instance 15 to 60 frames per second based on, for instance, a breathing rate of the subject 102 (e.g., where higher frame rates are used to capture faster breathing cycles (shallow inhales and exhales) by the subject 102 as compared to slower breathing cycles (e.g., deeper inhales and exhales) by the subject 102.

In the example of FIG. 1, the reflected or echo radar signals 110 detected by the antenna 105 are transmitted to heart rate detection circuitry 114. Also, the video frames 112 captured by the lower resolution sensor 106 are transmitted to the heart rate detection circuitry 114. The heart rate detection circuitry 114 serves to process the radar signals detected by the antenna 105 and the video frames 112 generated by the lower resolution sensor 106 to measure the heart rate for the subject 102. As disclosed herein, the heart rate detection circuitry 114 subtracts signal data associated with the video frames 112 from the radar echo signal data to generate signal data representing the heartbeat of the subject 102 to remove the effects of respiration (e.g., harmonics in the signal data due to respiration). The heart rate detection circuitry 114 uses the resulting signal data to determine the heart rate of the subject 102.

In the example of FIG. 1, the heart rate detection circuitry 114 analyzes the phases of the reflected signals 110 to verify that the signals 110 represent signals reflected by the subject 102 and not an inanimate object in the environment in which the subject 102 is located. The heart rate detection circuitry 114 can perform other operations such as filtering the signals 110 to increase a signal-to-noise ratio and phase unwrapping to address discontinuities in the signals 110.

The heart rate detection circuitry 114 of the illustrated example analyzes the video frames 112 to track changes in displacement of the chest 108 of the subject 102 due to respiration over time. In the example of FIG. 1, the heart rate detection circuitry 114 identifies a point (e.g., which may be represented by one or more pixels on a display) associated with the chest 108 of the subject in a first one of the video frame(s). The heart rate detection circuitry 114 identifies the coordinates of the chest point pixel(s). The heart rate detection circuitry 114 tracks the chest point pixel(s) over the subsequently collected video frames 112 to detect changes in the coordinates of the pixel(s) due to displacement of the chest 108 of the subject 102 during breathing. The heart rate detection circuitry 114 outputs a pixel value signal representing changes in the coordinates of the identified chest point pixel(s) over time.

The heart rate detection circuitry 114 of the illustrated example performs one or more joint signal processing techniques on the reflected signals 110 associated with the high resolution sensor 104 and the pixel-value signal associated with the video frames 112. For example, the heart rate detection circuitry 114 removes direct current (DC) components of the signals, which represent torso movements by the subject 102 (e.g., fidgeting during data collection). The heart rate detection circuitry 114 performs Short Time Fourier Transforms (STFT) on each of the signals 110 and the pixel value signal. The heart rate detection circuitry 114 performs harmonic cancellation to remove the effects of respiration from the signals 110 generated by the high resolution sensor 104. In particular, the heart rate detection circuitry 114 of this example subtracts the STFT spectrum generated for the pixel value signal from the STFT spectrum for the reflected signals 110 to remove the respiration harmonics. Thus, in the example of FIG. 1, image data (e.g., video frame data) generated by the lower resolution sensor 106 is used to remove harmonics due to respiration from the reflected signals 110 associated with the high resolution sensor 104. The resulting data includes signal data due to heartbeat without interference from signal data due to respiration. The example heart rate detection circuitry 114 measures (e.g., estimates, calculates) the heart rate of the subject 102 based on the signal data resulting after harmonic cancellation.

The heart rate detection circuitry 114 can be implemented by instructions executed on processor circuitry 116 of the electronic device 107, processor circuitry of another electronic device (e.g., a desktop, a smartphone, a wearable or non-wearable electronic device different than the electronic device 107), and/or on one or more cloud-based devices 118 (e.g., one or more server(s), processor(s), and/or virtual machine(s)). In some examples, some of the analysis performed by the heart rate detection circuitry 114 is implemented by the heart rate detection circuitry 114 via a cloud-computing environment and one or more other parts of the analysis is implemented by one or more of the dedicated logic circuitry of the electronic device 107, the processor circuitry 116, and/or the processor circuitry of a second electronic device (e.g., based on communication paths (e.g., via WiFi, cellular, Bluetooth®, and/or other communication protocols)).

Figure 2:
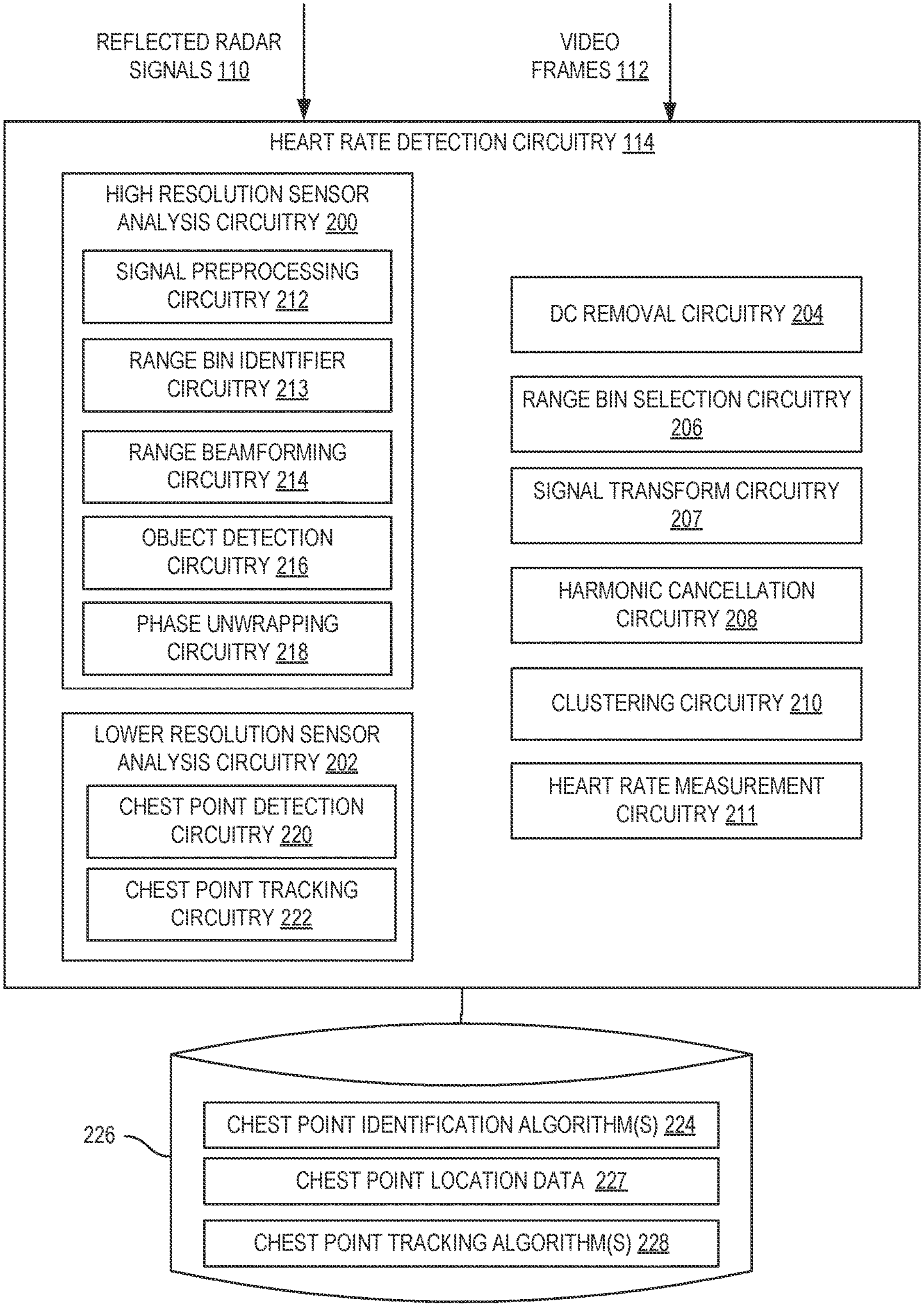
FIG. 2 is a block diagram of example heart rate detection circuitry.

FIG. 2 is a block diagram of an example implementation of the heart rate detection circuitry 114 of FIG. 1. The heart rate detection circuitry 114 is structured to measure (e.g., determine, calculate, estimate, predict) the heart rate of the subject 102 while accounting for the effects of respiration by the subject 102. The heart rate detection circuitry 114 of FIG. 2 may be instantiated (e.g., creating an instance of, bring into being for any length of time, materialize, implement, etc.) by processor circuitry such as a central processing unit executing instructions. Additionally or alternatively, the heart rate detection circuitry 114 of FIG. 2 may be instantiated (e.g., creating an instance of, bring into being for any length of time, materialize, implement, etc.) by an ASIC or an FPGA structured to perform operations corresponding to the instructions. It should be understood that some or all of the circuitry of FIG. 2 may, thus, be instantiated at the same or different times. Some or all of the circuitry may be instantiated, for example, in one or more threads executing concurrently on hardware and/or in series on hardware. Moreover, in some examples, some or all of the circuitry of FIG. 2 may be implemented by microprocessor circuitry executing instructions to implement one or more virtual machines and/or containers.

The example heart rate detection circuitry 114 of FIG. 2 includes high resolution sensor analysis circuitry 200, lower resolution sensor analysis circuitry 202, direct current (DC) removal circuitry 204, range bin selection circuitry 206, signal transform circuitry 207, harmonic cancellation circuitry 208, clustering circuitry 210, and heart rate measurement circuitry 211.

The example high resolution sensor analysis circuitry 200 of FIG. 2 includes signal preprocessing circuitry 212, range bin identifier circuitry 213, range beamforming circuitry 214, object detection circuitry 216, and phase unwrapping circuitry 218.

The example lower resolution sensor analysis circuitry 202 of FIG. 2 includes chest point detection circuitry 220 and chest point tracking circuitry 222.

Figure 17:
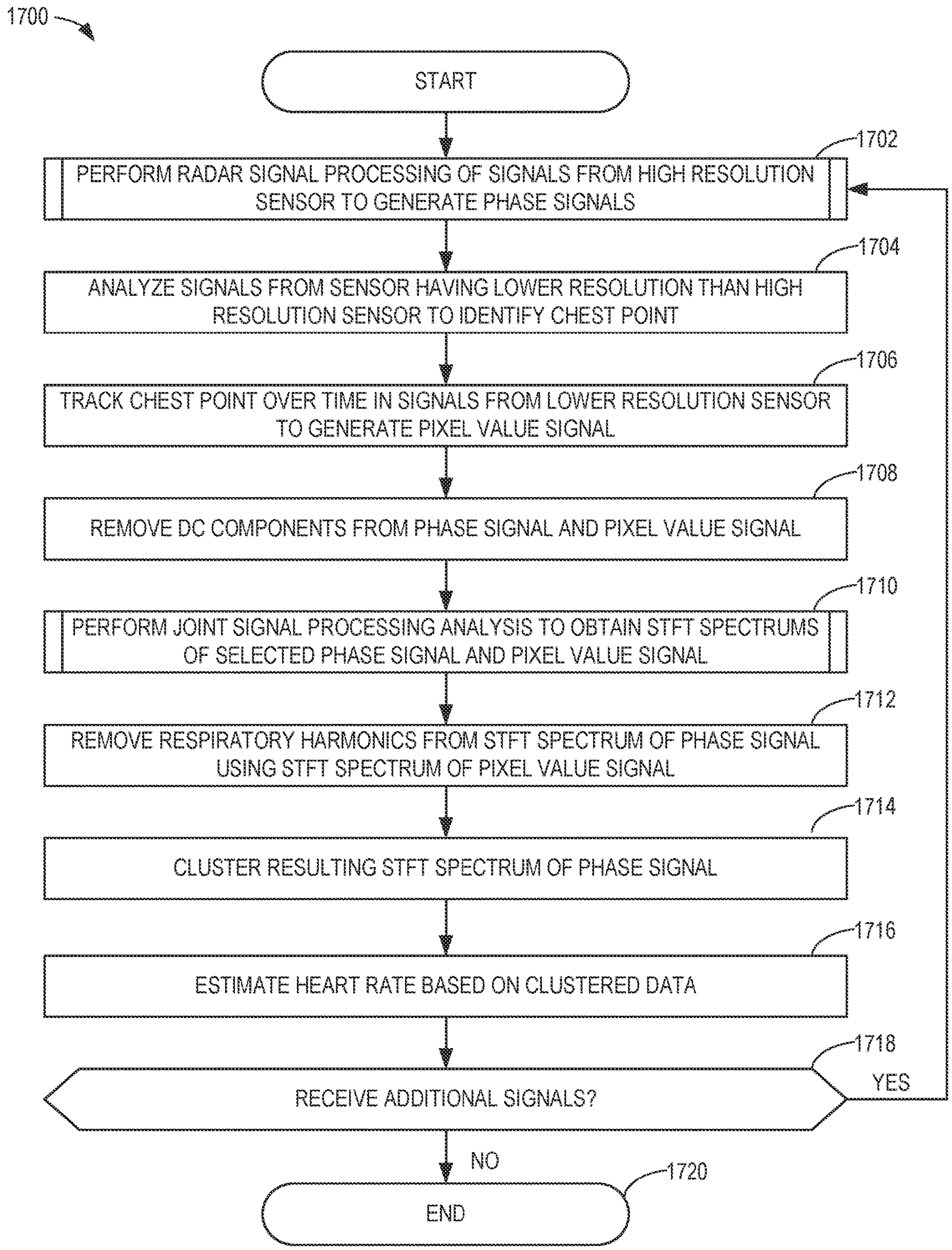
FIGS. 17-19 are flowcharts representative of example machine readable instructions and/or example operations that may be executed by example processor circuitry to implement the heart rate detection circuitry of FIG. 2.

In some examples, the high resolution sensor analysis circuitry 200 is instantiated by processor circuitry executing and/or configured by high resolution sensor instructions to perform operations such as those represented by the flowchart of FIGS. 17 and/or 18. In some examples, the lower resolution sensor analysis circuitry 202 is instantiated by processor circuitry executing and/or configured by lower resolution sensor instructions to perform operations such as those represented by the flowchart of FIG. 17. In some examples, the DC removal circuitry 204 is instantiated by processor circuitry executing and/or configured by DC removal instructions to perform operations such as those represented by the flowcharts of FIG. 17. In some examples, the range bin selection circuitry 206 is instantiated by processor circuitry executing and/or configured by range bin selection instructions to perform operations such as those represented by the flowcharts of FIGS. 17 and/or 19. In some examples, the signal transform circuitry 207 is instantiated by processor circuitry executing and/or configured by signal transform instructions to perform operations such as those represented by the flowcharts of FIGS. 17 and/or 19. In some examples, the harmonic cancellation circuitry 208 is instantiated by processor circuitry executing and/or configured by harmonic cancellation instructions to perform operations such as those represented by the flowchart of FIG. 17. In some examples, the clustering circuitry 210 is instantiated by processor circuitry executing and/or configured by clustering instructions to perform operations such as those represented by the flowchart of FIG. 17. In some examples, the heart rate measurement circuitry 211 is instantiated by processor circuitry executing and/or configured by clustering instructions to perform operations such as those represented by the flowchart of FIG. 17.

As shown in FIG. 2, the heart rate detection circuitry 114 accesses the reflected radar signals 110 (e.g., raw signal data) output by the high resolution sensor 104 of FIG. 1 and the video frames 112 generated by the lower resolution sensor 106. In some examples, the raw signal data 110 and/or the video frames 112 are stored in a database 226. In some examples, the heart rate detection circuitry 114 includes the database 226. In some examples, the database 226 is located external to the heart rate detection circuitry 114 in a location accessible to the heart rate detection circuitry 114 as shown in FIG. 2.

The high resolution sensor analysis circuitry 200 analyzes the reflected or echo radar signals 110 detected by the antenna 105. The signal preprocessing circuitry 212 can generate a radar data cube based on the signals detected from the multiple receiving channels of the antenna 105 to provide for time and spatial sampling of the radar signals 110.

The range bin identifier circuitry 213 of the high resolution sensor analysis circuitry 200 divides the ambient environment in which the antenna 105 is located into layers or bins, where the respective bins correspond to different distances from the antenna 105. The distances can be based on, for instance, millimeter ranges. In examples in which the antenna 105 is a multiple input, multiple output (MIMO), each range bin can include data from the multiple receiving channels of the antenna 105.

The range beamforming circuitry 214 of the high resolution sensor analysis circuitry 200 removes noise from the signals 110 to increase a signal-to-noise ratio of the signals. The range beamforming circuitry 214 implements signal processing techniques such as spatial filtering for the signals detected by the multiple receiving channels of the antenna 105.

The object detection circuitry 216 analyzes the signal data (e.g., radar data cube) corresponding to the reflected signals 110 to detect a presence of objects (e.g., the subject 102, an object such as furniture) in the environment. The radar signal emitted by the antenna 105 of the high resolution sensor 104 can be reflected by one or more objects in the environment such as the subject 102, a table at which the subject 102 is sitting, etc. The distance between an object that reflected the signal and the antenna 105 can be determined based on a time delay between (a) the time the signal was transmitted by the high resolution sensor 104 and (b) the time the signal 110 that was reflected by the object is detected by the antenna 105. In some examples, the presence of an object is represented by peaks in the signals 110. The object detection circuitry 216 analyzes the signal data to identify the range bins that are indicative of the presence of object(s) that have reflected the waves emitted by the high resolution sensor 104. In some examples, the object detection circuitry 216 executes one or more algorithms to reduce instances of false detection of the return echo signals received by the antenna 105 (e.g., Constant False Alarm Rate (CFAR)). In some examples, the object detection circuitry 216 executes one or more algorithms to group range bins associated with the same object (e.g., Density-Based Spatial Clustering of Application with Noise (DBSCAN). For instance, the presence of the subject 102 or an object such as a table may be associated with multiple range bins depending on the sensitivity of the range bins generated by the range bin identifier circuitry 213.

The phase unwrapping circuitry 218 of the high resolution sensor analysis circuitry 200 executes one or more algorithms to output phase signals for the range bins identified as associated with object presence (e.g., presence of the subject 102, presence of other objects) that include continuous signals. In some examples, the phase for the signals 110 may be limited to a range of $2\pi$. However, the phase of the signals 110 can be greater than the range of $2\pi$, which can lead to discontinuities in the signals 110 (e.g., a wrapped phase signal including a phase in a range of $(-7\pi, \pi]$). The phase wrapping circuitry 218 addresses discontinuities in the phase wrapped signals 110 (e.g., a phase jumps in the signal data) by returning the phase to a continuous signal (e.g., adding or subtracting $2\pi$ from the signal data). As a result of the phase unwrapping, the phase unwrapping circuitry 218 extracts the phase signal for the respective range bins in which objects are present.

The lower resolution sensor analysis circuitry 202 processes the video frames 112 output by the lower resolution sensor 106 (or other types of outputs of the sensor 106 based on the sensor type, e.g., ultrasound signals). The chest point detection circuitry 220 of the lower resolution sensor analysis circuitry 202 analyzes image data for a first one of the video frames 112 (e.g., a first video frame associated with time $t_1$) to select a point (e.g., pixel(s) on a display) associated with the chest 108 of the subject 102 in the image data. In particular, the chest point detection circuitry 220 selects one or more pixels corresponding to a location on the chest 108 of the subject 102 in the image data, referred to herein as chest point pixel(s). The chest point detection circuitry 220 identifies the coordinates of the chest point pixel(s) in the first video frame 112 (e.g., respective pixel coordinates (u, v)). The coordinates of the selected chest point pixel(s) can be stored in the database 226 as chest point location data 227.

The example chest point detection circuitry 220 of FIG. 2 executes one or more chest point identification algorithms 224 to identify the chest point pixel(s). In some examples, the chest point identification algorithm(s) 224 include machine learning algorithms to cause the chest point detection circuitry 220 to identify (e.g., recognize) the chest 108 of the subject 102 in the selected video frame 112 based on image analysis and to select one or more pixels associated with the image of the chest 108. In some examples, the chest point identification algorithm(s) 224 include human pose estimation model(s) that identify (e.g., estimate, predict) locations of joints of the subject 102 based on analysis of the image data and anthropometry (e.g., keypoint detection). In such examples, the chest point detection circuitry 220 calculates the coordinates of the chest point pixel(s) based on the coordinates of the pixels associated with the joints identified by the human pose estimation models. The chest point identification algorithm(s) 224 can be stored in the database 226.

The chest point tracking circuitry 222 of the lower resolution sensor analysis circuitry 202 receives the coordinates (e.g., (u, v)) of the selected chest point pixel(s) from the chest point detection circuitry 220. As disclosed herein, displacement of the chest 108 of the subject 102 can be due to variables such as torso movement, breathing, and heartbeat. The chest point tracking circuitry 222 executes one or more chest point tracking algorithms 228 to track changes in the pixel coordinate value of the selected chest point pixel(s) in the subsequent video frames 112 (e.g., a second video frame associated with time $t_1+1$, a third video frame associated with time $t_1+n$) generated by the lower resolution sensor 106 due to chest displacement. The chest point tracking algorithm(s) 228 can be stored in the database 226.

The chest point tracking algorithm(s) 228 can include, for example, a Kanade-Lucas-Tomasi (KLT) tracking algorithm to track displacement of the chest point pixel(s) between the respective video frames 112 based on (a) the coordinates of the chest point pixel(s) identified in the first video frame and (b) optical flow (e.g., a vector field between two video frames representing movement of pixels between the video frames). Based on the tracking, the chest point tracking algorithm(s) 228 predict the coordinates of the chest point pixel(s) in the subsequent video frames 112. The chest point tracking circuitry 222 store the updated coordinates of the chest point pixel(s) in the video frames 112 over time as the chest point location data 227. The chest point tracking circuitry 222 outputs a pixel value signal representing the changes of the coordinate values of the selected chest point pixel(s) over time (i.e., between the video frames 112).

In the example of FIG. 2, the heart rate detection circuitry 114 performs joint signal processing analysis of the phase signals for the range bins associated with object presence generated by the high resolution sensor analysis circuitry 200 and the pixel value signal output by the lower resolution sensor analysis circuitry 202. The example DC removal circuitry 204 of FIG. 2 removes the DC signal components or artifacts of the phase signals for the range bins. The DC removal circuitry 204 outputs DC-filtered phase signals. The DC removal circuitry 204 also removes the DC signal components or artifacts from the pixel value signal output by the lower resolution sensor analysis circuitry 202. The DC removal circuitry 204 outputs DC-filtered pixel value signal. The DC components in the signals are due to the movement of the chest of the user that is not due to breathing or heartbeat. For instance, the DC components of the phase signal associated with the high resolution sensor 104 can be due to fidgeting by the user during data collection, which results in torso movement. The DC removal circuitry 204 can execute a decomposition algorithm such a Variational Mode Decomposition (VIVID) algorithm to remove the DC components from the phase signals and the pixel value signal.

The range bin selection circuitry 206 identifies the range bins associated with the presence of the subject 102. In some examples, the range bin selection circuitry 206 differentiates between phase signals associated with human subjects, which likely include a modulated phase, and phase signals associated with inanimate objects in the environment, which typically include a static phase. In the example of FIG. 2, the range bin selection circuitry 206 uses the DC-filtered pixel value signal to select the range bin mostly closely associated with portion of the chest 108 of the subject 102 including the chest point pixel selected by the chest point detection circuitry 220. For example, the range bin selection circuitry 206 selects the range bin for which the DC-filtered phase signal has a maximum correlation with the DC-filtered pixel value signal (e.g., where correlation refers to a mutual relationship between the DC-filtered phase signal and the DC-filtered pixel signal). Selecting the range bin that has the maximum correlation with DC-filtered pixel value signal can enhance the quality of the phase signal of the selected range bin. Such selection of the range bin based on the maximum correlation with DC-filtered pixel value signal provides can provide a faster and more reliable approach to selecting the range bin associated with the chest 108 than other approaches, such as SoTA range bin selection algorithms that select the range bin based on empirical features of the phase signal itself.

The signal transform circuitry 207 normalizes the DC-filtered phase signal associated with the range bin identified by the range bin selection circuitry 206 and the DC-filtered pixel value signal. The signal transform circuitry 207 performs a Short-time Fourier transform (STFT) for the DC-filtered phase signal associated with the range bin identified by the range bin selection circuitry 206. The signal transform circuitry 207 also performs STFT for the DC-filtered pixel value signal. The signal transform circuitry 207 can perform the STFT for segments of the respective signals spanning 10 seconds, 20 seconds, etc.

The resulting STFT spectrum for the phase signal associated with the high resolution sensor 104 can include harmonics (e.g., high order harmonics) due to respiration by the subject 102. The harmonic cancellation circuitry 208 of the example heart rate detection circuitry 114 of FIG. 2 removes the respiratory harmonics from the STFT spectrum for the phase signal associated with the high resolution sensor 104. In particular, the harmonic cancellation circuitry 208 subtracts the STFT of the pixel-value signal from the STFT of the phase signal. As a result, harmonics associated with respiration are removed or cancelled from the high resolution sensor phase signal. The resulting signal data represents the heartbeat of the subject 102. Thus, in the example of FIG. 2, the heart rate detection circuitry 114 uses the low-resolution sensor data (e.g., the video frames 112) to remove respiratory harmonics that could otherwise affect the detection of the heart rate of the subject 102.

The clustering circuitry 210 of the heart rate detection circuitry 114 executes one or more clustering algorithms (e.g., DBSCAN algorithm) to cluster the resulting heartbeat signal that results from harmonic cancellation performed by the harmonic cancellation circuitry 208 (e.g., the subtraction of the STFT of the pixel-value signal from the STFT of the phase signal).

The example heart rate measurement circuitry 211 of FIG. 2 measures (e.g., determines, calculates, estimates) the heart rate of the subject 102 based on an average of the signal components within a cluster of the signal data. Because the respiratory harmonics have been removed from the signal data, the risk that signal components associated with respiration are treated as heartbeat data by the heart rate measurement circuitry 211 is eliminated. Thus, the output by the heart rate measurement circuitry 211 accurately represents the heart rate (e.g., beats per minute) of the subject 102.

In some examples, the heart rate detection circuitry 114 includes means for analyzing high resolution sensor signals. For example, the means for analyzing high resolution sensor signals may be implemented by high resolution sensor circuitry 200. In some examples, the high resolution sensor circuitry 200 may be instantiated by processor circuitry such as the example processor circuitry 2012 of FIG. 20. For instance, the high resolution sensor circuitry 200 may be instantiated by the example microprocessor 2100 of FIG. 21 executing machine executable instructions such as those implemented by at least blocks 1702 of FIG. 17 and/or blocks 1800, 1802, 1804, 1806, and/or 1808 of FIG. 18. In some examples, the high resolution sensor circuitry 200 may be instantiated by hardware logic circuitry, which may be implemented by an ASIC, XPU, or the FPGA circuitry 2200 of FIG. 22 structured to perform operations corresponding to the machine readable instructions. Additionally or alternatively, the high resolution sensor circuitry 200 may be instantiated by any other combination of hardware, software, and/or firmware. For example, the high resolution sensor circuitry 200 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the means for analyzing high resolution sensor signals includes means for preprocessing signals, means for range bin generation, means for range beamforming, means for object detection, and means for phase unwrapping.

In some examples, the heart rate detection circuitry 114 includes means for detecting a chest point. For example, the means for detecting a chest point may be implemented by chest point detection circuitry 220. In some examples, the chest point detection circuitry 220 may be instantiated by processor circuitry such as the example processor circuitry 2012 of FIG. 20. For instance, the chest point circuitry 220 may be instantiated by the example microprocessor 2100 of FIG. 21 executing machine executable instructions such as those implemented by at least block 1704 of FIG. 17. In some examples, the chest point detection circuitry 220 may be instantiated by hardware logic circuitry, which may be implemented by an ASIC, XPU, or the FPGA circuitry 2200 of FIG. 22 structured to perform operations corresponding to the machine readable instructions. Additionally or alternatively, the chest point detection circuitry 220 may be instantiated by any other combination of hardware, software, and/or firmware. For example, the chest point detection circuitry 220 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the heart rate detection circuitry 114 includes means for tracking. For example, the means for tracking may be implemented by chest point tracking circuitry 222. In some examples, the chest point tracking circuitry 222 may be instantiated by processor circuitry such as the example processor circuitry 2012 of FIG. 20. For instance, the chest point tracking circuitry 222 may be instantiated by the example microprocessor 2100 of FIG. 21 executing machine executable instructions such as those implemented by at least block 1706 of FIG. 17. In some examples, the chest point tracking circuitry 222 may be instantiated by hardware logic circuitry, which may be implemented by an ASIC, XPU, or the FPGA circuitry 2200 of FIG. 22 structured to perform operations corresponding to the machine readable instructions. Additionally or alternatively, the chest point tracking circuitry 222 may be instantiated by any other combination of hardware, software, and/or firmware. For example, the chest point tracking circuitry 222 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the heart rate detection circuitry 114 includes means for removing DC signal components. For example, the means for removing DC signal components may be implemented by the DC removal circuitry 204. In some examples, the DC removal circuitry 204 may be instantiated by processor circuitry such as the example processor circuitry 2012 of FIG. 20. For instance, the DC removal circuitry 204 may be instantiated by the example microprocessor 2100 of FIG. 21 executing machine executable instructions such as those implemented by at least block 1708 of FIG. 17. In some examples, the DC removal circuitry 204 may be instantiated by hardware logic circuitry, which may be implemented by an ASIC, XPU, or the FPGA circuitry 2200 of FIG. 22 structured to perform operations corresponding to the machine readable instructions. Additionally or alternatively, the DC removal circuitry 204 may be instantiated by any other combination of hardware, software, and/or firmware. For example, the DC removal circuitry 204 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the heart rate detection circuitry 114 includes means for range bin selecting. For example, the means for range bin selecting may be implemented by the range bin selection circuitry 206. In some examples, the range bin selection circuitry 206 may be instantiated by processor circuitry such as the example processor circuitry 2012 of FIG. 20. For instance, the range bin selection circuitry 206 may be instantiated by the example microprocessor 2100 of FIG. 21 executing machine executable instructions such as those implemented by at least blocks 1710 of FIG. 17 and/or block 1900 of FIG. 19. In some examples, the range bin selection circuitry 206 may be instantiated by hardware logic circuitry, which may be implemented by an ASIC, XPU, or the FPGA circuitry 2200 of FIG. 22 structured to perform operations corresponding to the machine readable instructions. Additionally or alternatively, the range bin selection circuitry 206 may be instantiated by any other combination of hardware, software, and/or firmware. For example, the range bin selection circuitry 206 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the heart rate detection circuitry 114 includes means for signal transforming. For example, the means for signal transforming may be implemented by the signal transform circuitry 207. In some examples, the signal transform circuitry 207 may be instantiated by processor circuitry such as the example processor circuitry 2012 of FIG. 20. For instance, the signal transform circuitry 207 may be instantiated by the example microprocessor 2100 of FIG. 21 executing machine executable instructions such as those implemented by at least blocks 1710 of FIG. 17 and/or blocks 1902, 1904 of FIG. 19. In some examples, the signal transform circuitry 207 may be instantiated by hardware logic circuitry, which may be implemented by an ASIC, XPU, or the FPGA circuitry 2200 of FIG. 22 structured to perform operations corresponding to the machine readable instructions. Additionally or alternatively, the signal transform circuitry 207 may be instantiated by any other combination of hardware, software, and/or firmware. For example, the signal transform circuitry 207 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the heart rate detection circuitry 114 includes means for cancelling harmonics. For example, the means for cancelling harmonics may be implemented by the harmonics cancellation circuitry 208. In some examples, the harmonics cancellation circuitry 208 may be instantiated by processor circuitry such as the example processor circuitry 2012 of FIG. 20. For instance, the harmonics cancellation circuitry 208 may be instantiated by the example microprocessor 2100 of FIG. 21 executing machine executable instructions such as those implemented by at least block 1712 of FIG. 17. In some examples, the harmonics cancellation circuitry 208 may be instantiated by hardware logic circuitry, which may be implemented by an ASIC, XPU, or the FPGA circuitry 2200 of FIG. 22 structured to perform operations corresponding to the machine readable instructions. Additionally or alternatively, the harmonics cancellation circuitry 208 may be instantiated by any other combination of hardware, software, and/or firmware. For example, the harmonics cancellation circuitry 208 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the heart rate detection circuitry 114 includes means for clustering. For example, the means for clustering may be implemented by the clustering circuitry 210. In some examples, the clustering circuitry 210 may be instantiated by processor circuitry such as the example processor circuitry 2012 of FIG. 20. For instance, the clustering circuitry 210 may be instantiated by the example microprocessor 2100 of FIG. 21 executing machine executable instructions such as those implemented by at least block 1714 of FIG. 17. In some examples, the clustering circuitry 210 may be instantiated by hardware logic circuitry, which may be implemented by an ASIC, XPU, or the FPGA circuitry 2200 of FIG. 22 structured to perform operations corresponding to the machine readable instructions. Additionally or alternatively, the clustering circuitry 210 may be instantiated by any other combination of hardware, software, and/or firmware. For example, the clustering circuitry 210 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

In some examples, the heart rate detection circuitry 114 includes means for measuring heart rate. For example, the means for measuring heart rate may be implemented by the heart rate measurement circuitry 211. In some examples, the heart rate measurement circuitry 211 may be instantiated by processor circuitry such as the example processor circuitry 2012 of FIG. 20. For instance, the heart rate measurement circuitry 211 may be instantiated by the example microprocessor 2100 of FIG. 21 executing machine executable instructions such as those implemented by at least block 1716 of FIG. 17. In some examples, the heart rate measurement circuitry 211 may be instantiated by hardware logic circuitry, which may be implemented by an ASIC, XPU, or the FPGA circuitry 2200 of FIG. 22 structured to perform operations corresponding to the machine readable instructions. Additionally or alternatively, the heart rate measurement circuitry 211 may be instantiated by any other combination of hardware, software, and/or firmware. For example, the heart rate measurement circuitry 211 may be implemented by at least one or more hardware circuits (e.g., processor circuitry, discrete and/or integrated analog and/or digital circuitry, an FPGA, an ASIC, an XPU, a comparator, an operational-amplifier (op-amp), a logic circuit, etc.) structured to execute some or all of the machine readable instructions and/or to perform some or all of the operations corresponding to the machine readable instructions without executing software or firmware, but other structures are likewise appropriate.

While an example manner of implementing the heart rate detection circuitry 114 of FIG. 1 is illustrated in FIG. 2, one or more of the elements, processes, and/or devices illustrated in FIG. 2 may be combined, divided, re-arranged, omitted, eliminated, and/or implemented in any other way. Further, the example high resolution sensor analysis circuitry 200, the example signal preprocessing circuitry 212, the example range bin identifier circuitry 213, the example range beamforming circuitry 214, the example object detection circuitry 216, the example phase unwrapping circuitry 218, the example lower resolution sensor analysis circuitry 202, the example chest point detection circuitry 220, the example chest point tracking circuitry 222, the example DC removal circuitry 204, the range bin selection circuitry 206, the example signal transform circuitry 207, the example harmonic cancellation circuitry 208, the example clustering circuitry 210, and the example heart rate measurement circuitry 211, and/or, more generally, the example heart rate detection circuitry 114 of FIG. 1, may be implemented by hardware alone or by hardware in combination with software and/or firmware. Thus, for example, any of the example high resolution sensor analysis circuitry 200, the example signal preprocessing circuitry 212, the example range bin identifier circuitry 213, the example range beamforming circuitry 214, the example object detection circuitry 216, the example phase unwrapping circuitry 218, the example lower resolution sensor analysis circuitry 202, the example chest point detection circuitry 220, the example chest point tracking circuitry 222, the example DC removal circuitry 204, the range bin selection circuitry 206, the example signal transform circuitry 207, the example harmonic cancellation circuitry 208, the example clustering circuitry 210, and the example heart rate measurement circuitry 211, and/or, more generally, the example heart rate detection circuitry 114, could be implemented by processor circuitry, analog circuit(s), digital circuit(s), logic circuit(s), programmable processor(s), programmable microcontroller(s), graphics processing unit(s) (GPU(s)), digital signal processor(s) (DSP(s)), application specific integrated circuit(s) (ASIC(s)), programmable logic device(s) (PLD(s)), and/or field programmable logic device(s) (FPLD(s)) such as Field Programmable Gate Arrays (FPGAs). Further still, the example heart rate detection circuitry 114 of FIG. 1 may include one or more elements, processes, and/or devices in addition to, or instead of, those illustrated in FIG. 2, and/or may include more than one of any or all of the illustrated elements, processes and devices.

Figure 3:
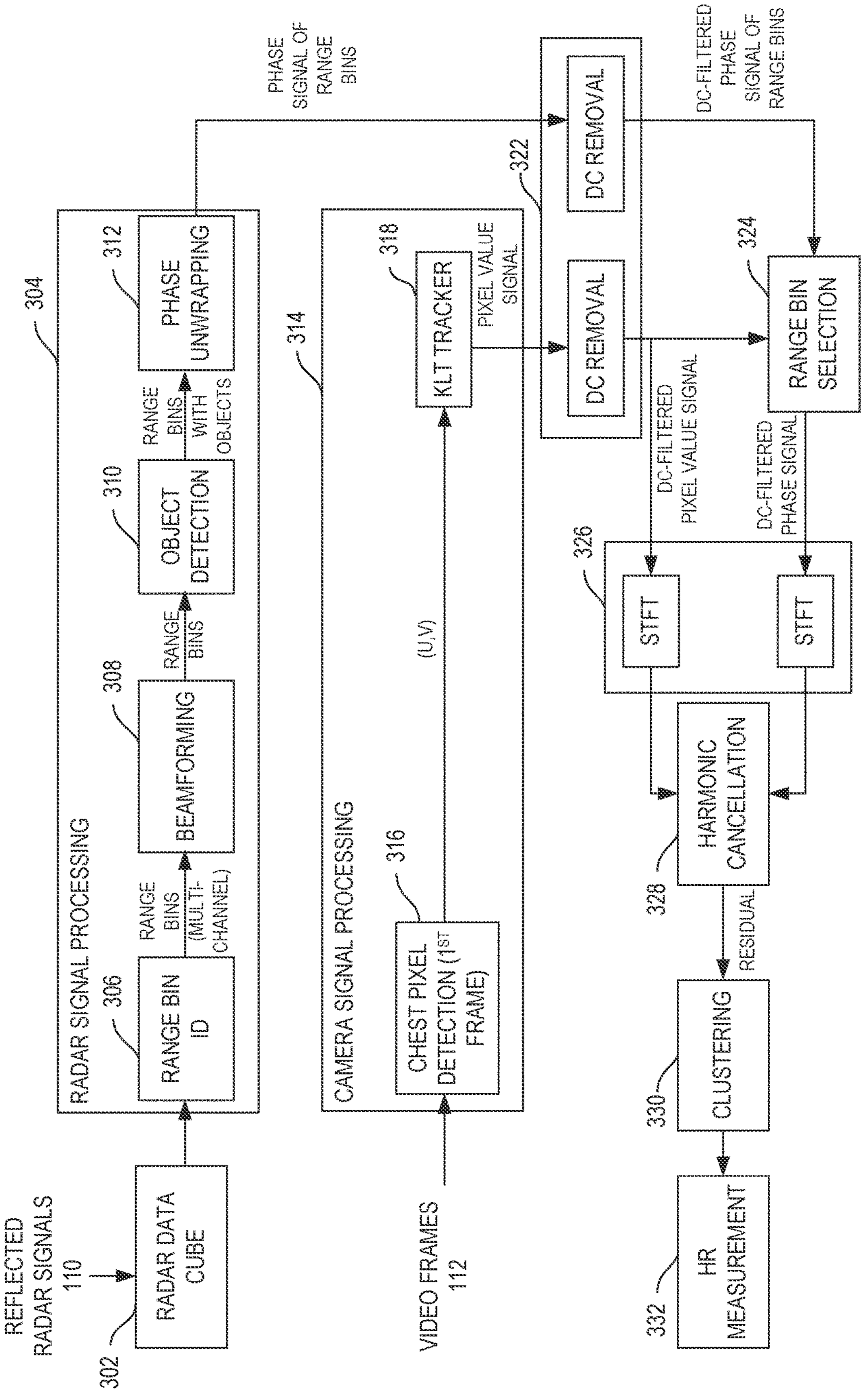
FIG. 3 is an example signal processing flow diagram in accordance with teachings of this disclosure.

FIG. 3 is a flow diagram 300 illustrating example signal processing and analysis of the outputs of the high resolution sensor 104 and the lower resolution sensor 106 of FIG. 1 by the example heart rate detection circuitry 114 of FIG. 2. For example, the signal preprocessing circuitry 212 generates a radar data cube based on the reflected radar signals 110 received by the antenna 105 of the high resolution sensor 104 of FIG. 1 (block 302). The high resolution sensor analysis circuitry 200 of the example heart rate detection circuitry 114 of FIG. 2 performs radar signal processing for radar data cube corresponding to the signals 110, as represented by block 304 in FIG. 3. The range bin identifier circuitry 213 generates range bins for the environment in which the subject 102 is located (block 306). The range beamforming circuitry 214 increases the signal-to-noise ratio in the signals (block 308). The object detection circuitry 216 identifies range bins for which presence of an object (e.g., the subject 102, furniture) is detected (block 310). The phase unwrapping circuitry 218 extracts the phase signal for the range bins in which an object is present (block 312). As shown in FIG. 3, the high resolution sensor analysis circuitry 200 outputs phase signals for the respective range bins for which object presence has been detected.

As shown in FIG. 3, the lower resolution sensor analysis circuitry 202 of the example heart rate detection circuitry 114 of FIG. 2 performs camera signal processing for the video frames 112 generated by the lower resolution sensor 106 of FIG. 1, as represented by block 314 in FIG. 3. With respect to the camera signal processing, the chest point detection circuitry 220 identifies coordinates (u, v) of one or more chest point pixel(s) in one of the video frames 112 (block 316). The chest point tracking circuitry 222 tracks the coordinates of the chest point pixel(s) in subsequent video frames 112 (block 318). The chest point tracking circuitry 222 outputs a pixel value signal including the coordinates of the chest point pixel(s) over time.

The example flow diagram 300 of FIG. 3 include joint signal processing of the outputs of the high resolution sensor analysis circuitry 200 and the outputs of the lower resolution sensor analysis circuitry 202. As shown in FIG. 3, the DC removal circuitry 204 removes the DC component from the phase signals for the range bin and the pixel value signal (block 322). The range bin selection circuitry 206 uses the DC-filtered phase signals and the DC-filtered pixel value signal to identify the range bin in which the subject is located and, in particular, the range bin closest to the chest point pixel detected by the chest point detection circuitry 220 (block 324).

The signal transform circuitry 207 normalizes the DC-filtered phase signal for the selected range bin associated with the subject presence and the DC-filtered pixel value signal and performs Short Time Fourier Transform for each signal (block 326). The harmonic cancellation circuitry 208 subtracts the DC-filtered pixel value signal from the DC-filtered phase signal to remove harmonics associated with respiration from the phase signal (block 328). The clustering circuitry 210 clusters the resulting signal (block 330). The heart rate measurement circuitry 211 determines (e.g., estimates) the heart rate based on the signal data in the cluster (block 332).

Figure 4:
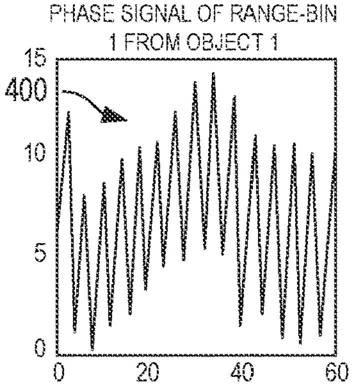
FIGS. 4-16 are graphs showing example signal analysis in accordance with teachings of this disclosure.
Figure 5:
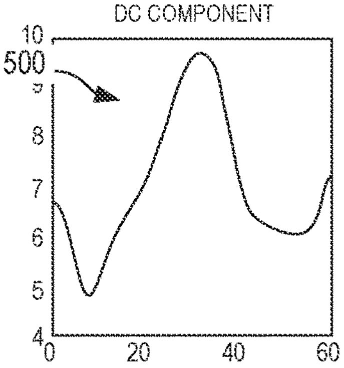
Figure 6:
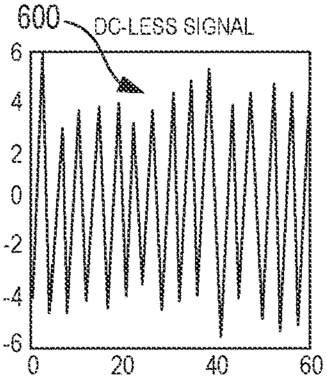

FIGS. 4-16 include example graphs illustrating the signal analysis performed by the example heart rate detection circuitry 114. FIG. 4 illustrates a phase signal 400 associated with a first range bin in which the subject 102 of FIG. 1 is detected (e.g., by the object detection circuitry 216 of FIG. 2). The first range bin can be associated with a radar signal reflected from a first location of the chest 108 of the subject 102 (e.g., proximate to a right side of the subject's chest). FIG. 5 illustrates a DC component 500 of the phase signal 400 due to, for instance, torso movement by the subject 102 during data collection. In FIG. 6, the DC component 500 has been removed from the phase signal 400 to generate a DC-filtered phase signal 600.

Figure 7:
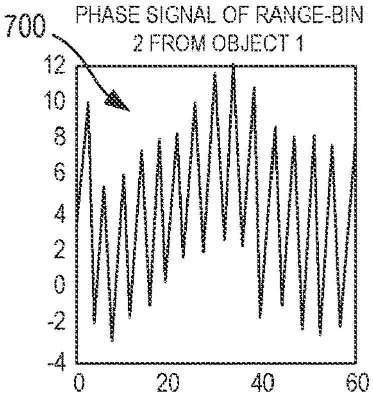
Figure 8:
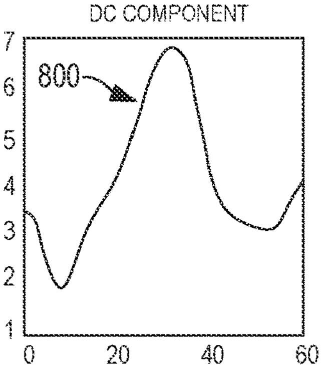
Figure 9:
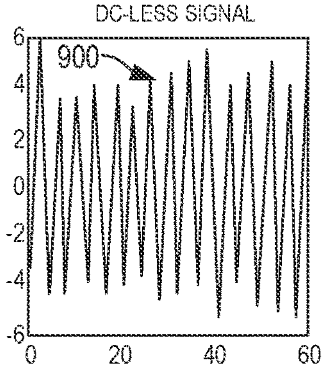

FIGS. 7-9 illustrate a phase signal 700, DC component 800 of the phase signal 700, and a DC-filtered phase signal 900 for a second range bin in which the subject 102 is detected e.g., by the object detection circuitry 216 of FIG. 2). The second range bin can be associated with a radar signal reflected from a second location of the chest 108 of the subject 102 different than the first location discussed in connection with FIGS. 4-6 (e.g., proximate to a left side of the subject's chest).

Figure 10:
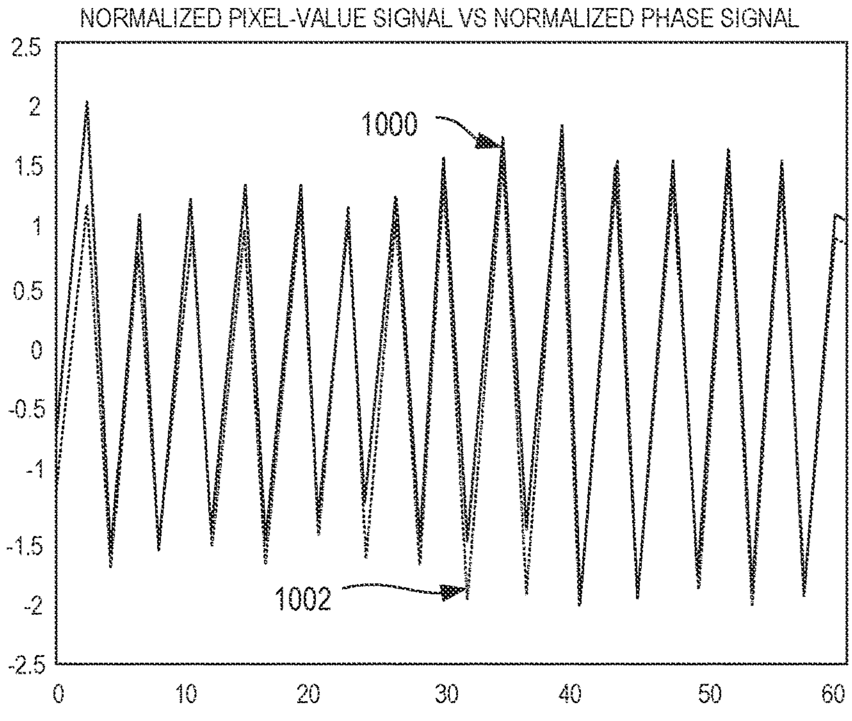

FIG. 10 is a graph showing a normalized DC-filtered phase signal 1000 and a normalized DC-filtered pixel value signal 1002 (e.g., generated by the signal transform circuitry 207). In particular, the normalized signals 1000,1002 of FIG. 10 are the resulting normalized signals after (a) the DC removal circuitry 204 has removed the DC component from the phase signals output by the high resolution sensor 104 and the pixel value signal output by the lower resolution sensor 106 and (b) after the range bin selection circuitry 206 has selected a range bin associated with the phase signal as the range bin closest to the selected chest point pixel.

Figure 11:
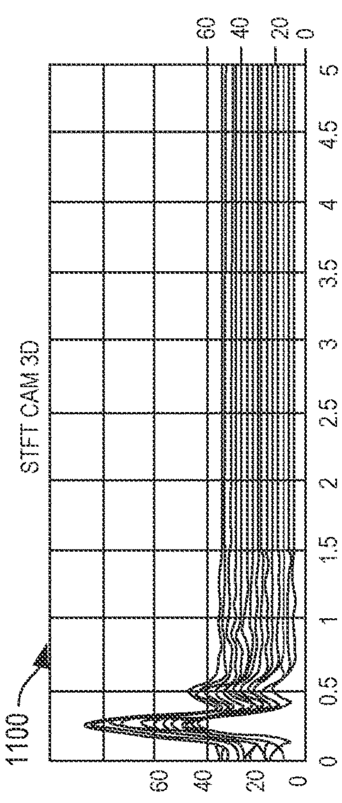
Figure 12:
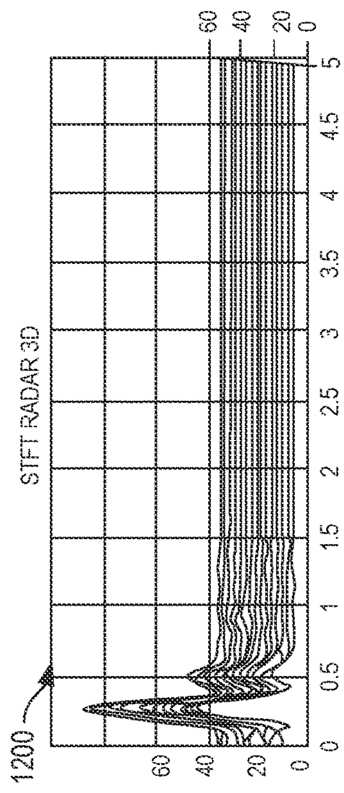
Figure 13:
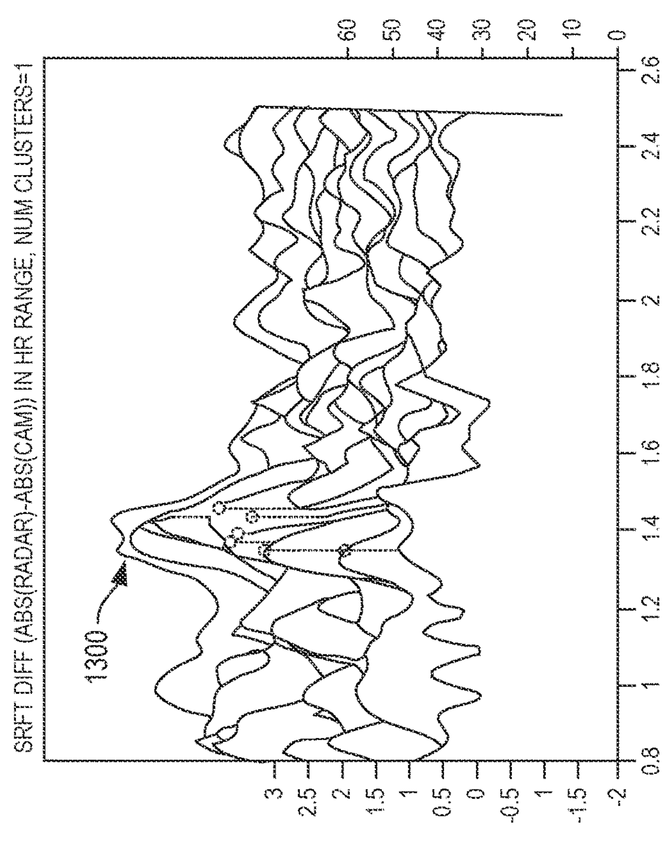

FIG. 11 is a plot of the STFT spectrum 1100 for the normalized DC-filtered pixel value signal 1000 generated as a result of the STFT analysis performed by the signal transform circuitry 207. FIG. 12 is a plot of the STFT spectrum 1200 for the normalized DC-filtered phase signal 1002 of FIG. 10 generated as a result of the STFT analysis performed by the signal transform circuitry 207. FIG. 13 illustrates the result of clustering of the STFT spectrum of the DC-filtered phase signal 1000 performed by the clustering circuitry 210 after the harmonic cancellation circuitry 208 has subtracted the STFT spectrum of the DC-filtered pixel value signal 1002 from the STFT spectrum of the DC-filtered phase signal 1000. The example of FIG. 13 includes one cluster 1300 representative of the heartbeat signal. The cluster 1300 is indicative of heartbeats of the subject 102 over the sliding windows that are used to perform the STFT spectrums (e.g., 10 second windows). The heart rate measurement circuitry 211 uses the cluster 1300 to estimate heart rate (e.g., by averaging the heartbeat data in the cluster 1300).

Figure 14:
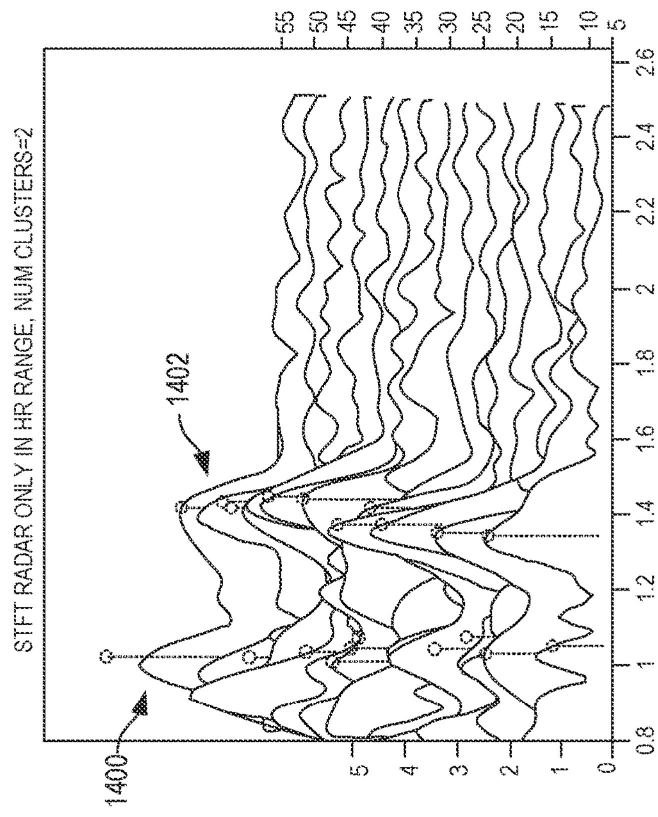

For comparative purposes, FIG. 14 illustrates the result of clustering of the STFT spectrum of the DC-filtered phase signal 1000 without subtracting the STFT spectrum of the DC-filtered pixel value signal 1002 from the STFT spectrum of the DC-filtered phase signal 1000. Put another way, in the plot of FIG. 13, the harmonics due to respiration have been removed, while in the plot of FIG. 14, the harmonics due to respiration have not been removed. As shown in FIG. 14, without harmonic cancellation, a first cluster 1400 and a second cluster 1402 may be identified by the heart rate measurement circuitry 211 as a heartbeat signals (e.g., based on amplitude, frequency, etc.). However, the first cluster 1400 is associated with respiratory harmonics. The first cluster 1400 includes higher peaks than the second cluster 1402 due to a larger amount of chest displacement from respiration than heartbeat. Thus, the heart rate measurement circuitry 211 may erroneously select the first cluster 1400 as the heartbeat signal for determining heart rate.

Conversely, in the example of FIG. 13, the respiratory harmonics (e.g., signal artifacts) have been removed as a result of subtracting the STFT spectrum of the DC-filtered pixel value signal 1002 from the STFT spectrum of the DC-filtered phase signal 1000. Thus, the example of FIG. 13 includes the one cluster 1300 representative of the heartbeat signal. As a result, the cluster 1300 used by the heart rate measurement circuitry 211 to measure (e.g., determine, estimate) the heart rate of the subject 102 accurately reflects the subject's heart rate without interference from respiration. Therefore, examples disclosed herein use resolution differences between the sensors 104, 106 to cancel the respiratory harmonics.

Figure 16:
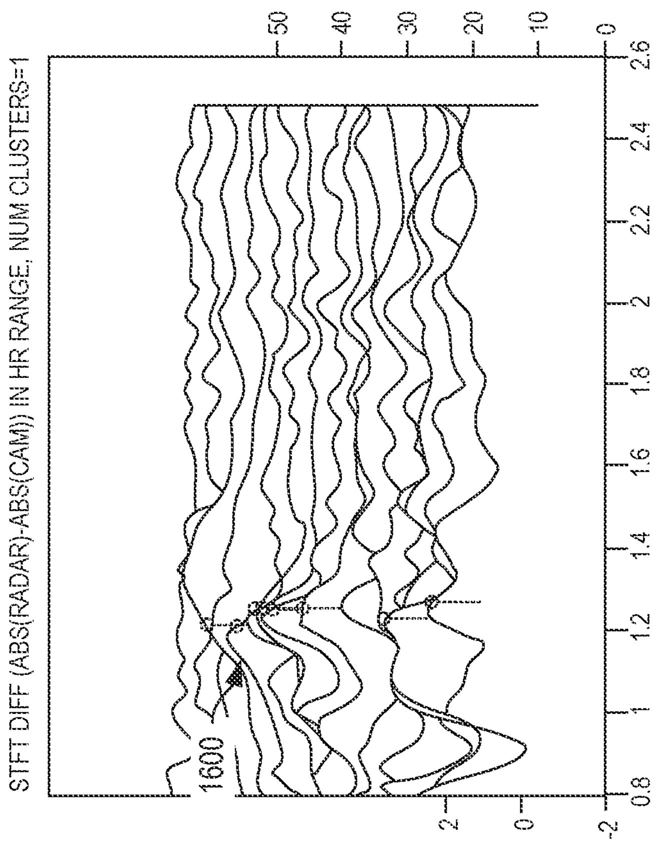
Figure 15:
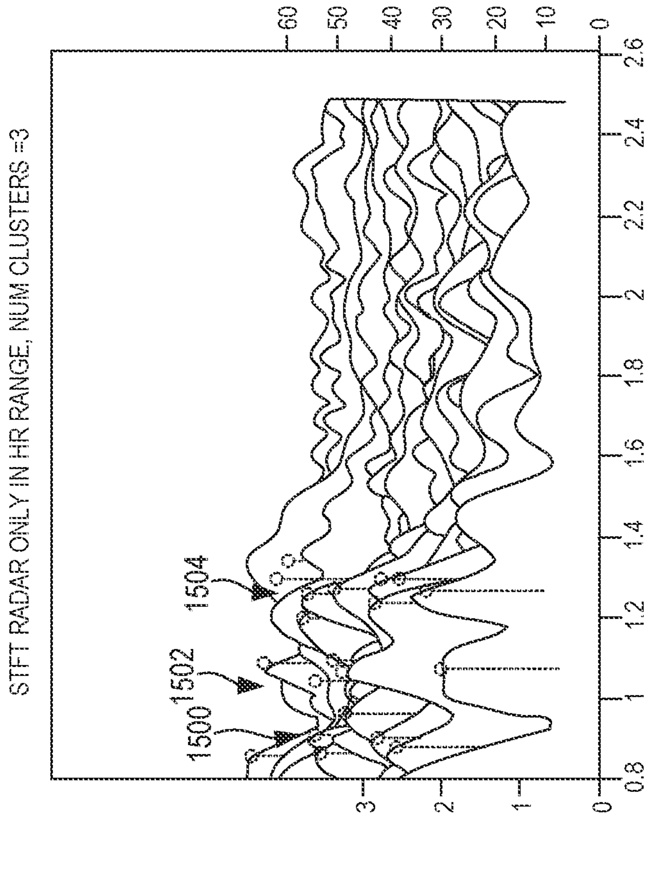

In the examples of FIGS. 4-14, the subject 102 may be breathing regular or substantially regular inhalations and exhalations. FIGS. 15 and 16 show the results of clustering signal data collected when the subject 102 is breathing irregularly, such as holding his or her breath. FIG. 15 illustrates the result of clustering of the STFT spectrum of the DC-filtered phase signal without subtracting the STFT spectrum of the DC-filtered pixel value signal from the STFT spectrum of the DC-filtered phase signal, where the subject 102 is holding his or her breath for several seconds. As shown in FIG. 15, three clusters 1500, 1502, 1504 may be identified by the heart rate measurement circuitry 211 as representing the heartbeat signal (e.g., based on amplitude, frequency, etc.). However, in actuality, the irregular respiration has caused more respiratory harmonics to appear in the signal data due to the high-order components of the irregular signal.

FIG. 16 shows the results of clustering after harmonic cancellation performed by the harmonic cancellation circuitry 208, in which the STFT spectrum of the DC-filtered phase signal are subtracted from the STFT spectrum of the DC-filtered pixel value signal from the STFT spectrums of the DC-filtered phase signal. As shown in FIG. 16, one cluster 1600 representative of the heartbeat signal results from the clustering performed by the clustering circuitry 210. As such, examples disclosed herein use the data generated by the lower resolution sensor 106 to remove respiratory harmonics that would otherwise interfere with detection of the heartbeat signal and, thus, determination of the heart rate of the subject 102.

Figure 18:
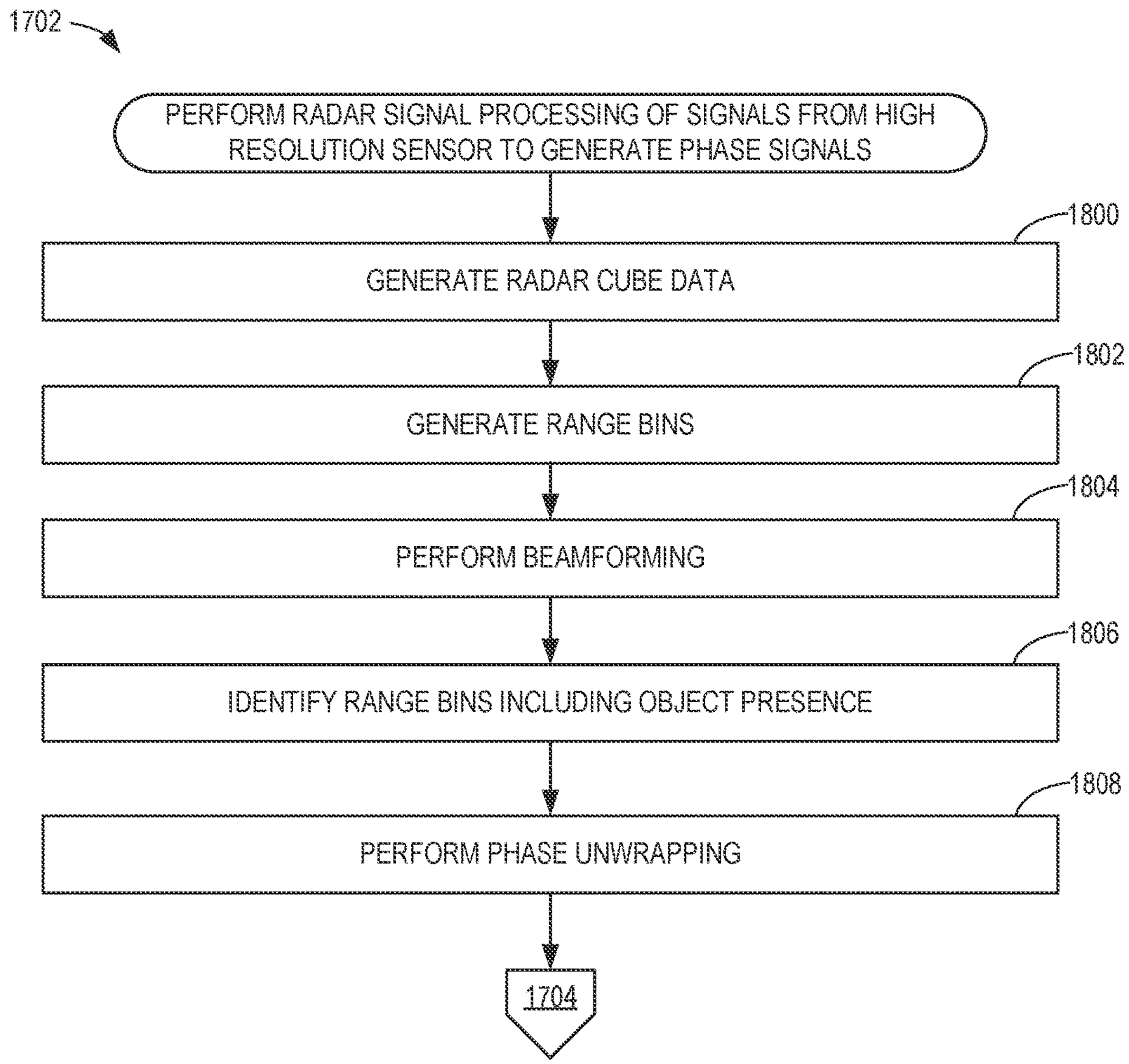
Figure 19:
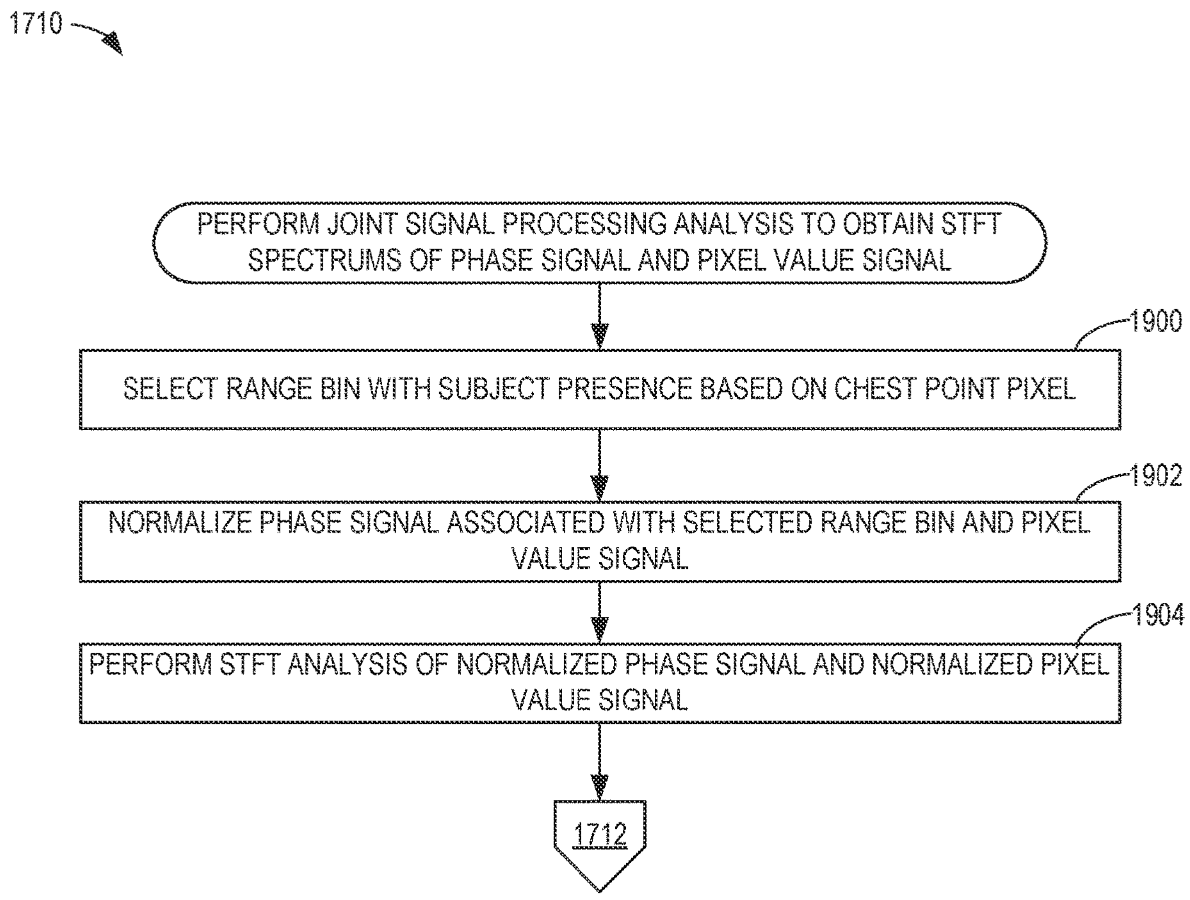

Flowcharts representative of example machine readable instructions, which may be executed to configure processor circuitry to implement the heart rate detection circuitry 114 of FIG. 2, are shown in FIGS. 17-19. The machine readable instructions may be one or more executable programs or portion(s) of an executable program for execution by processor circuitry, such as the processor circuitry 2012 shown in the example processor platform 2000 discussed below in connection with FIG. 20 and/or the example processor circuitry discussed below in connection with FIGS. 21 and/or 22. The program may be embodied in software stored on one or more non-transitory computer readable storage media such as a compact disk (CD), a floppy disk, a hard disk drive (HDD), a solid-state drive (SSD), a digital versatile disk (DVD), a Blu-ray disk, a volatile memory (e.g., Random Access Memory (RAM) of any type, etc.), or a non-volatile memory (e.g., electrically erasable programmable read-only memory (EEPROM), FLASH memory, an HDD, an SSD, etc.) associated with processor circuitry located in one or more hardware devices, but the entire program and/or parts thereof could alternatively be executed by one or more hardware devices other than the processor circuitry and/or embodied in firmware or dedicated hardware. The machine readable instructions may be distributed across multiple hardware devices and/or executed by two or more hardware devices (e.g., a server and a client hardware device). For example, the client hardware device may be implemented by an endpoint client hardware device (e.g., a hardware device associated with a user) or an intermediate client hardware device (e.g., a radio access network (RAN)) gateway that may facilitate communication between a server and an endpoint client hardware device). Similarly, the non-transitory computer readable storage media may include one or more mediums located in one or more hardware devices. Further, although the example program is described with reference to the flowcharts illustrated in FIGS. 17-19, many other methods of implementing the example heart rate detection circuitry 114 may alternatively be used. For example, the order of execution of the blocks may be changed, and/or some of the blocks described may be changed, eliminated, or combined. Additionally or alternatively, any or all of the blocks may be implemented by one or more hardware circuits (e.g., processor circuitry, discrete and/or integrated analog and/or digital circuitry, an FPGA, an ASIC, a comparator, an operational-amplifier (op-amp), a logic circuit, etc.) structured to perform the corresponding operation without executing software or firmware. The processor circuitry may be distributed in different network locations and/or local to one or more hardware devices (e.g., a single-core processor (e.g., a single core central processor unit (CPU)), a multi-core processor (e.g., a multi-core CPU, an XPU, etc.) in a single machine, multiple processors distributed across multiple servers of a server rack, multiple processors distributed across one or more server racks, a CPU and/or a FPGA located in the same package (e.g., the same integrated circuit (IC) package or in two or more separate housings, etc.).

The machine readable instructions described herein may be stored in one or more of a compressed format, an encrypted format, a fragmented format, a compiled format, an executable format, a packaged format, etc. Machine readable instructions as described herein may be stored as data or a data structure (e.g., as portions of instructions, code, representations of code, etc.) that may be utilized to create, manufacture, and/or produce machine executable instructions. For example, the machine readable instructions may be fragmented and stored on one or more storage devices and/or computing devices (e.g., servers) located at the same or different locations of a network or collection of networks (e.g., in the cloud, in edge devices, etc.). The machine readable instructions may require one or more of installation, modification, adaptation, updating, combining, supplementing, configuring, decryption, decompression, unpacking, distribution, reassignment, compilation, etc., in order to make them directly readable, interpretable, and/or executable by a computing device and/or other machine. For example, the machine readable instructions may be stored in multiple parts, which are individually compressed, encrypted, and/or stored on separate computing devices, wherein the parts when decrypted, decompressed, and/or combined form a set of machine executable instructions that implement one or more operations that may together form a program such as that described herein.

In another example, the machine readable instructions may be stored in a state in which they may be read by processor circuitry, but require addition of a library (e.g., a dynamic link library (DLL)), a software development kit (SDK), an application programming interface (API), etc., in order to execute the machine readable instructions on a particular computing device or other device. In another example, the machine readable instructions may need to be configured (e.g., settings stored, data input, network addresses recorded, etc.) before the machine readable instructions and/or the corresponding program(s) can be executed in whole or in part. Thus, machine readable media, as used herein, may include machine readable instructions and/or program(s) regardless of the particular format or state of the machine readable instructions and/or program(s) when stored or otherwise at rest or in transit.

The machine readable instructions described herein can be represented by any past, present, or future instruction language, scripting language, programming language, etc. For example, the machine readable instructions may be represented using any of the following languages: C, C++, Java, C #, Perl, Python, JavaScript, HyperText Markup Language (HTML), Structured Query Language (SQL), Swift, etc.

As mentioned above, the example operations of FIGS. 17-19 may be implemented using executable instructions (e.g., computer and/or machine readable instructions) stored on one or more non-transitory computer and/or machine readable media such as optical storage devices, magnetic storage devices, an HDD, a flash memory, a read-only memory (ROM), a CD, a DVD, a cache, a RAM of any type, a register, and/or any other storage device or storage disk in which information is stored for any duration (e.g., for extended time periods, permanently, for brief instances, for temporarily buffering, and/or for caching of the information). As used herein, the terms non-transitory computer readable medium, non-transitory computer readable storage medium, non-transitory machine readable medium, and non-transitory machine readable storage medium are expressly defined to include any type of computer readable storage device and/or storage disk and to exclude propagating signals and to exclude transmission media. As used herein, the terms "computer readable storage device" and "machine readable storage device" are defined to include any physical (mechanical and/or electrical) structure to store information, but to exclude propagating signals and to exclude transmission media. Examples of computer readable storage devices and machine readable storage devices include random access memory of any type, read only memory of any type, solid state memory, flash memory, optical discs, magnetic disks, disk drives, and/or redundant array of independent disks (RAID) systems. As used herein, the term "device" refers to physical structure such as mechanical and/or electrical equipment, hardware, and/or circuitry that may or may not be configured by computer readable instructions, machine readable instructions, etc., and/or manufactured to execute computer readable instructions, machine readable instructions, etc.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc., may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, or (7) A with B and with C. As used herein in the context of describing structures, components, items, objects and/or things, the phrase "at least one of A and B" is intended to refer to implementations including any of (1) at least one A, (2) at least one B, or (3) at least one A and at least one B. Similarly, as used herein in the context of describing structures, components, items, objects and/or things, the phrase "at least one of A or B" is intended to refer to implementations including any of (1) at least one A, (2) at least one B, or (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, or (3) at least one A and at least one B. Similarly, as used herein in the context of describing the performance or execution of processes, instructions, actions, activities and/or steps, the phrase "at least one of A or B" is intended to refer to implementations including any of (1) at least one A, (2) at least one B, or (3) at least one A and at least one B.

As used herein, singular references (e.g., "a," "an," "first," "second," etc.) do not exclude a plurality. The term "a" or "an" object, as used herein, refers to one or more of that object. The terms "a" (or "an"), "one or more," and "at least one" are used interchangeably herein. Furthermore, although individually listed, a plurality of means, elements or method actions may be implemented by, e.g., the same entity or object. Additionally, although individual features may be included in different examples or claims, these may possibly be combined, and the inclusion in different examples or claims does not imply that a combination of features is not feasible and/or advantageous.

FIG. 17 is a flowchart representative of example machine readable instructions and/or example operations 1700 that may be executed and/or instantiated by processor circuitry to measure (e.g., estimate, determine, calculate) heart rate of a subject such as the subject 102 of FIG. 1. The machine readable instructions and/or the operations 1700 of FIG. 17 begin at block 1702, at which the high resolution sensor analysis circuitry 200 analyzes reflected radar signals 110 received by the antenna 105 of the high resolution sensor 104 in response to transmission of waves by the transmitter 103. The high resolution sensor analysis circuitry 200 generates phase signals, as disclosed in connection with FIG. 18.

At block 1704, the chest point detection circuitry 220 of the lower resolution sensor analysis circuitry 202 selects a point on the chest 108 of the subject 102 for tracking. For instance, the chest point can correspond to one or more pixel(s) having respective coordinates (u, v) in a video frame 112 generated by the lower resolution sensor 106. At block 1706, the chest point tracking circuitry 222 tracks the location (e.g., coordinates) of the chest point in subsequent signals from the lower resolution sensor 106 (e.g., subsequent video frames) to generate a pixel value signal.

At block 1708, the DC removal circuitry 204 removes the DC component from the phase signals and the pixel value signal and, thus, removes the effects of torso movements by the subject 102 from the data.

At block 1710, the range bin selection circuitry 206 and the signal transform circuitry 207 perform joint signal processing for the phase signals and the pixel value signal, as disclosed in connection with FIG. 19. As a result of the joint signal processing, the signal transform circuitry 207 generates an STFT spectrum of the phase signal associated with a particular range binge selected by the range bin selection circuitry 206. The signal transform circuitry 207 also generates a STFT spectrum of the pixel value signal.

At block 1712, the harmonic cancellation circuitry 208 removes the respiratory harmonics from the STFT spectrum of the phase signal using the STFT spectrum of the pixel value signal. For example, the harmonic cancellation circuitry 208 subtracts the STFT spectrum of the pixel value signal from the STFT spectrum of the phase signal.

At block 1714, the clustering circuitry 210 clusters the STFT spectrum of the phase signal that results after the harmonic cancellation.

At block 1716, the heart rate measurement circuitry 211 estimates the heart rate of the subject 102 based on the clustered signal data, where the cluster(s) in the signal data represent heartbeat of the subject 102. The example instructions 1700 of FIG. 17 end when there is no further signal data to analyze (blocks 1718, 1720).

FIG. 18 is a flowchart representative of the example machine readable instructions and/or example operations 1702 that may be executed and/or instantiated by processor circuitry to perform radar signal processing of reflected radar signals 110 received by the antenna 105 of the high resolution sensor 104 to generate phase signals. At block 1800, the signal preprocessing circuitry 212 generates radar cube data based on the echo signals 110 received by the antenna 105. At block 1802, the range bin identifier circuitry 213 generates range bins that divide the ambient environment in which the subject 102 is located into bins based on distance from the antenna 105 of the high resolution sensor 104. At block 1804, the range beamforming circuitry 214 performs beamforming of the signals associated with the range bins to increase the signal-to-noise ratio. At block 1806, the object detection circuitry 216 identifies range bins for which the presence of objects (e.g., the subject 102, other individuals and/or furniture) in the environment is detected. At block 1808, the phase unwrapping circuitry 218 performs unwrapping of the signal data to provide for continuous phase signals associated with the range bins. Control proceeds to block 1704 of FIG. 17.

FIG. 19 is a flowchart representative of the example machine readable instructions and/or example operations 1710 that may be executed and/or instantiated by processor circuitry to perform joint signal processing analysis to obtain STFT spectrums of the phase signal and the pixel value signal. At block 1900, the range bin selection circuitry 206 selects the range bin associated with the presence of the subject 102 based on, for example, the location of the chest point pixel(s) as represented by the pixel value signal. At block 1902, the signal transform circuitry 207 normalizes the phase signal associated with the selected range bin and the pixel value signal. At block 1906, the signal transform circuitry 207 performs an STFT analysis of the normalized phase signal and the normalized pixel value signal. Control proceeds to block 1712 of FIG. 17.

Figure 20:
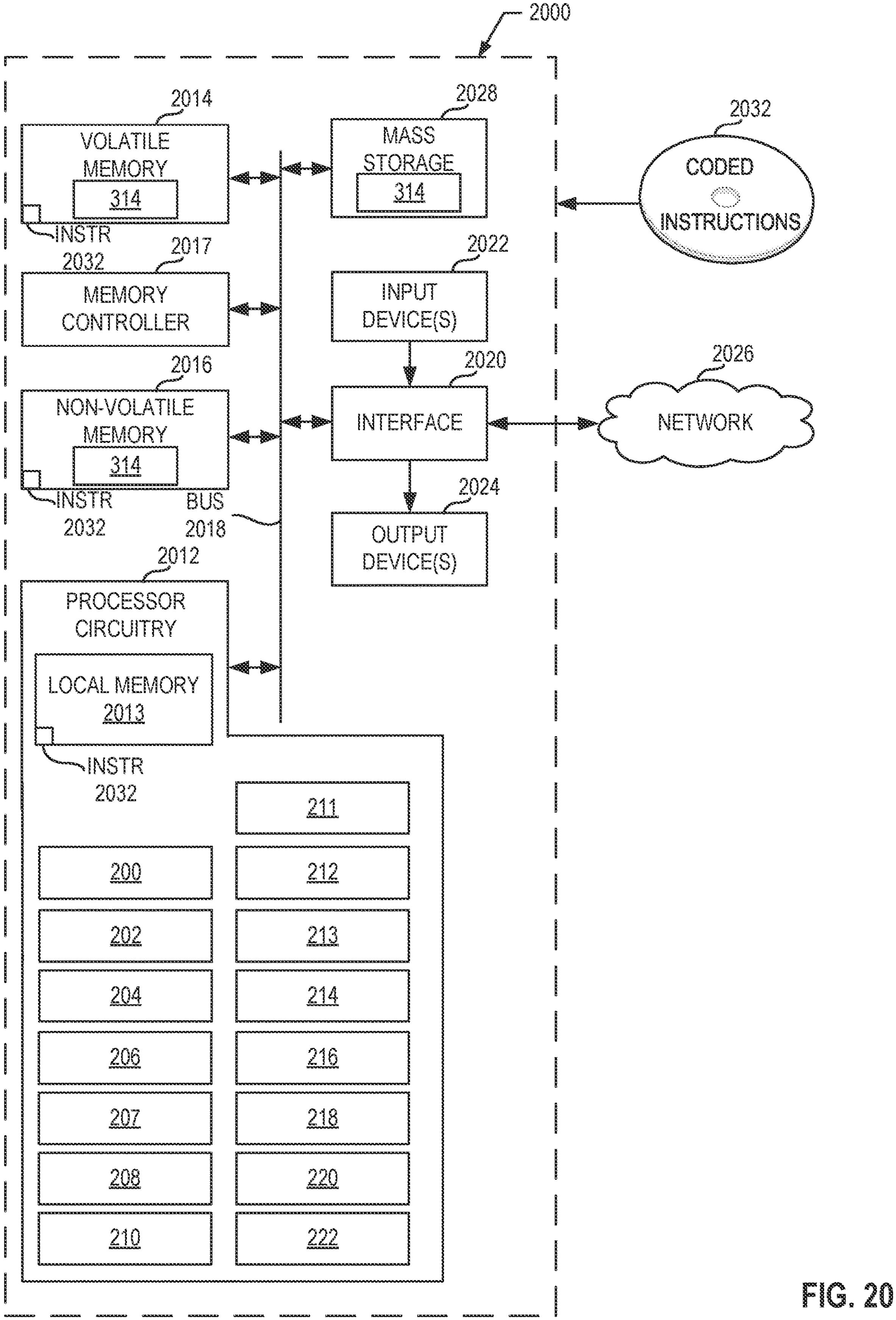
FIG. 20 is a block diagram of an example processing platform including processor circuitry structured to execute the example machine readable instructions and/or the example operations of FIGS. 17-19 to implement the heart rate detection circuitry of FIG. 2.

FIG. 20 is a block diagram of an example processor platform 2000 structured to execute and/or instantiate the machine readable instructions and/or the operations of FIGS. 17-19 to implement the heart rate detection circuitry 114 of FIG. 2. The processor platform 2000 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, or any other type of computing device.

The processor platform 2000 of the illustrated example includes processor circuitry 2012. The processor circuitry 2012 of the illustrated example is hardware. For example, the processor circuitry 2012 can be implemented by one or more integrated circuits, logic circuits, FPGAs, microprocessors, CPUs, GPUs, DSPs, and/or microcontrollers from any desired family or manufacturer. The processor circuitry 2012 may be implemented by one or more semiconductor based (e.g., silicon based) devices. In this example, the processor circuitry 2012 implements the example high resolution sensor analysis circuitry 200, the example signal preprocessing circuitry 212, the example range bin identifier circuitry 213, the example range beamforming circuitry 214, the example object detection circuitry 216, the example phase unwrapping circuitry 218, the example lower resolution sensor analysis circuitry 202, the example chest point detection circuitry 220, the example chest point tracking circuitry 222, the example DC removal circuitry 204, the range bin selection circuitry 206, the example signal transform circuitry 207, the example harmonic cancellation circuitry 208, the example clustering circuitry 210, and the example heart rate measurement circuitry 211.

The processor circuitry 2012 of the illustrated example includes a local memory 2013 (e.g., a cache, registers, etc.). The processor circuitry 2012 of the illustrated example is in communication with a main memory including a volatile memory 2014 and a non-volatile memory 2016 by a bus 2018. The volatile memory 2014 may be implemented by Synchronous Dynamic Random Access Memory (SDRAM), Dynamic Random Access Memory (DRAM), RAMBUS® Dynamic Random Access Memory (RDRAM®), and/or any other type of RAM device. The non-volatile memory 2016 may be implemented by flash memory and/or any other desired type of memory device. Access to the main memory 2014, 2016 of the illustrated example is controlled by a memory controller 2017.

The processor platform 2000 of the illustrated example also includes interface circuitry 2020. The interface circuitry 2020 may be implemented by hardware in accordance with any type of interface standard, such as an Ethernet interface, a universal serial bus (USB) interface, a Bluetooth® interface, a near field communication (NFC) interface, a Peripheral Component Interconnect (PCI) interface, and/or a Peripheral Component Interconnect Express (PCIe) interface.

In the illustrated example, one or more input devices 2022 are connected to the interface circuitry 2020. The input device(s) 2022 permit(s) a user to enter data and/or commands into the processor circuitry 2012. The input device(s) 2022 can be implemented by, for example, an audio sensor, a microphone, a camera (still or video), a keyboard, a button, a mouse, a touchscreen, a track-pad, a trackball, an isopoint device, and/or a voice recognition system.

One or more output devices 2024 are also connected to the interface circuitry 2020 of the illustrated example. The output device(s) 2024 can be implemented, for example, by display devices (e.g., a light emitting diode (LED), an organic light emitting diode (OLED), a liquid crystal display (LCD), a cathode ray tube (CRT) display, an in-place switching (IPS) display, a touchscreen, etc.), a tactile output device, a printer, and/or speaker. The interface circuitry 2020 of the illustrated example, thus, typically includes a graphics driver card, a graphics driver chip, and/or graphics processor circuitry such as a GPU.

The interface circuitry 2020 of the illustrated example also includes a communication device such as a transmitter, a receiver, a transceiver, a modem, a residential gateway, a wireless access point, and/or a network interface to facilitate exchange of data with external machines (e.g., computing devices of any kind) by a network 2026. The communication can be by, for example, an Ethernet connection, a digital subscriber line (DSL) connection, a telephone line connection, a coaxial cable system, a satellite system, a line-of-site wireless system, a cellular telephone system, an optical connection, etc.

The processor platform 2000 of the illustrated example also includes one or more mass storage devices 2028 to store software and/or data. Examples of such mass storage devices 2028 include magnetic storage devices, optical storage devices, floppy disk drives, HDDs, CDs, Blu-ray disk drives, redundant array of independent disks (RAID) systems, solid state storage devices such as flash memory devices and/or SSDs, and DVD drives.

The machine readable instructions 2032, which may be implemented by the machine readable instructions of FIGS. 17-19, may be stored in the mass storage device 2028, in the volatile memory 2014, in the non-volatile memory 2016, and/or on a removable non-transitory computer readable storage medium such as a CD or DVD.

Figure 21:
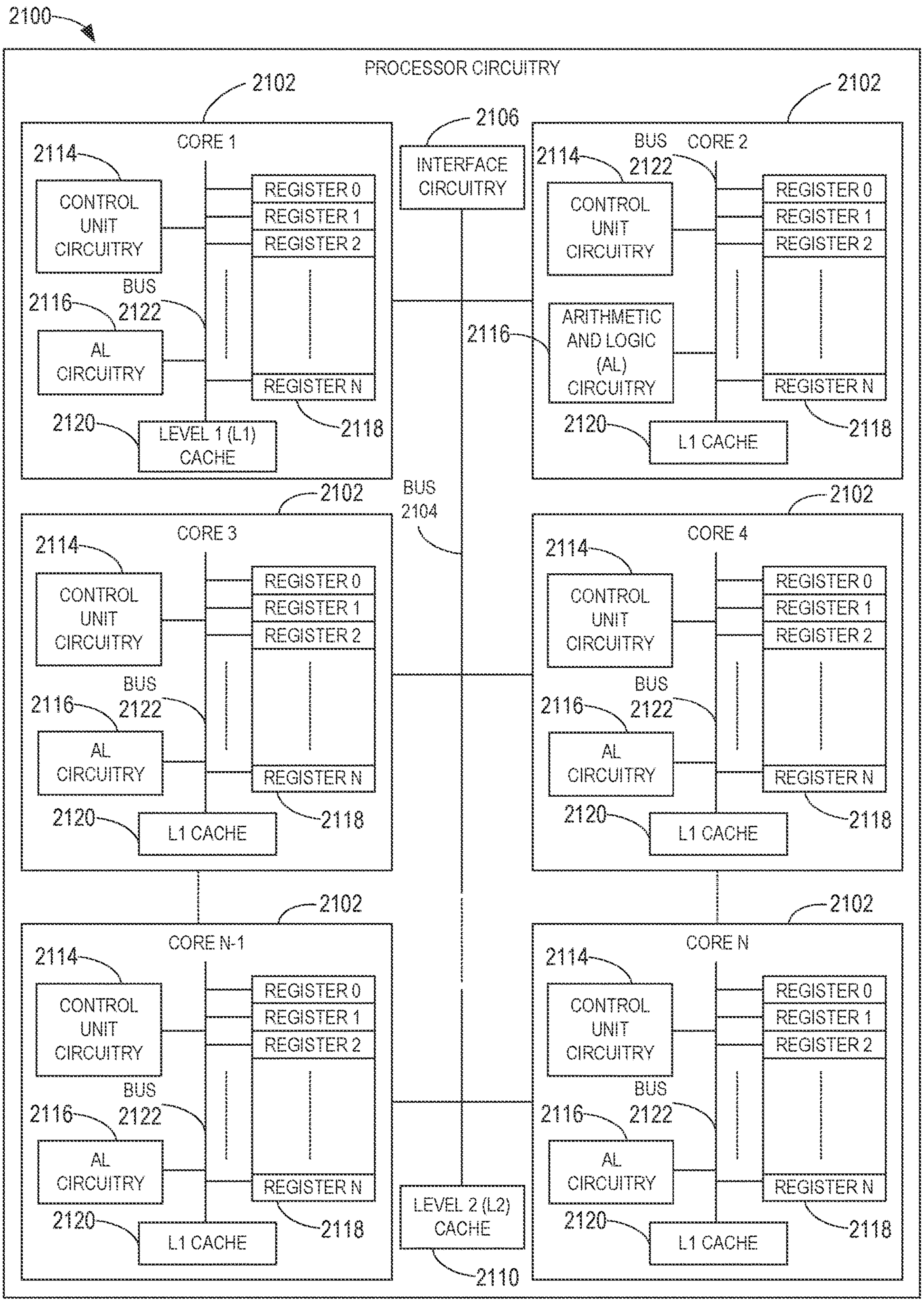
FIG. 21 is a block diagram of an example implementation of the processor circuitry of FIG. 20.

FIG. 21 is a block diagram of an example implementation of the processor circuitry 2012 of FIG. 20. In this example, the processor circuitry 2012 of FIG. 20 is implemented by a microprocessor 2100. For example, the microprocessor 2100 may be a general purpose microprocessor (e.g., general purpose microprocessor circuitry). The microprocessor 2100 executes some or all of the machine readable instructions of the flowcharts of FIGS. 17-19 to effectively instantiate the circuitry of FIG. 2 as logic circuits to perform the operations corresponding to those machine readable instructions. In some such examples, the circuitry of FIG. 2 is instantiated by the hardware circuits of the microprocessor 2100 in combination with the instructions. For example, the microprocessor 2100 may be implemented by multi-core hardware circuitry such as a CPU, a DSP, a GPU, an XPU, etc. Although it may include any number of example cores 2102 (e.g., 1 core), the microprocessor 2100 of this example is a multi-core semiconductor device including N cores. The cores 2102 of the microprocessor 2100 may operate independently or may cooperate to execute machine readable instructions. For example, machine code corresponding to a firmware program, an embedded software program, or a software program may be executed by one of the cores 2102 or may be executed by multiple ones of the cores 2102 at the same or different times. In some examples, the machine code corresponding to the firmware program, the embedded software program, or the software program is split into threads and executed in parallel by two or more of the cores 2102. The software program may correspond to a portion or all of the machine readable instructions and/or operations represented by the flowcharts of FIGS. 17-19.

The cores 2102 may communicate by a first example bus 2104. In some examples, the first bus 2104 may be implemented by a communication bus to effectuate communication associated with one(s) of the cores 2102. For example, the first bus 2104 may be implemented by at least one of an Inter-Integrated Circuit (I2C) bus, a Serial Peripheral Interface (SPI) bus, a PCI bus, or a PCIe bus. Additionally or alternatively, the first bus 2104 may be implemented by any other type of computing or electrical bus. The cores 2102 may obtain data, instructions, and/or signals from one or more external devices by example interface circuitry 2106. The cores 2102 may output data, instructions, and/or signals to the one or more external devices by the interface circuitry 2106. Although the cores 2102 of this example include example local memory 2120 (e.g., Level 1 (L1) cache that may be split into an L1 data cache and an L1 instruction cache), the microprocessor 2100 also includes example shared memory 2110 that may be shared by the cores (e.g., Level 2 (L2 cache)) for high-speed access to data and/or instructions. Data and/or instructions may be transferred (e.g., shared) by writing to and/or reading from the shared memory 2110. The local memory 2120 of each of the cores 2102 and the shared memory 2110 may be part of a hierarchy of storage devices including multiple levels of cache memory and the main memory (e.g., the main memory 2014, 2016 of FIG. 20). Typically, higher levels of memory in the hierarchy exhibit lower access time and have smaller storage capacity than lower levels of memory. Changes in the various levels of the cache hierarchy are managed (e.g., coordinated) by a cache coherency policy.

Each core 2102 may be referred to as a CPU, DSP, GPU, etc., or any other type of hardware circuitry. Each core 2102 includes control unit circuitry 2114, arithmetic and logic (AL) circuitry (sometimes referred to as an ALU) 2116, a plurality of registers 2118, the local memory 2120, and a second example bus 2122. Other structures may be present. For example, each core 2102 may include vector unit circuitry, single instruction multiple data (SIMD) unit circuitry, load/store unit (LSU) circuitry, branch/jump unit circuitry, floating-point unit (FPU) circuitry, etc. The control unit circuitry 2114 includes semiconductor-based circuits structured to control (e.g., coordinate) data movement within the corresponding core 2102. The AL circuitry 2116 includes semiconductor-based circuits structured to perform one or more mathematic and/or logic operations on the data within the corresponding core 2102. The AL circuitry 2116 of some examples performs integer based operations. In other examples, the AL circuitry 2116 also performs floating point operations. In yet other examples, the AL circuitry 2116 may include first AL circuitry that performs integer based operations and second AL circuitry that performs floating point operations. In some examples, the AL circuitry 2116 may be referred to as an Arithmetic Logic Unit (ALU). The registers 2118 are semiconductor-based structures to store data and/or instructions such as results of one or more of the operations performed by the AL circuitry 2116 of the corresponding core 2102. For example, the registers 2118 may include vector register(s), SIMD register(s), general purpose register(s), flag register(s), segment register(s), machine specific register(s), instruction pointer register(s), control register(s), debug register(s), memory management register(s), machine check register(s), etc. The registers 2118 may be arranged in a bank as shown in FIG. 21. Alternatively, the registers 2118 may be organized in any other arrangement, format, or structure including distributed throughout the core 2102 to shorten access time. The second bus 2122 may be implemented by at least one of an I2C bus, a SPI bus, a PCI bus, or a PCIe bus Each core 2102 and/or, more generally, the microprocessor 2100 may include additional and/or alternate structures to those shown and described above. For example, one or more clock circuits, one or more power supplies, one or more power gates, one or more cache home agents (CHAs), one or more converged/common mesh stops (CMSs), one or more shifters (e.g., barrel shifter(s)) and/or other circuitry may be present. The microprocessor 2100 is a semiconductor device fabricated to include many transistors interconnected to implement the structures described above in one or more integrated circuits (ICs) contained in one or more packages. The processor circuitry may include and/or cooperate with one or more accelerators. In some examples, accelerators are implemented by logic circuitry to perform certain tasks more quickly and/or efficiently than can be done by a general purpose processor. Examples of accelerators include ASICs and FPGAs such as those discussed herein. A GPU or other programmable device can also be an accelerator. Accelerators may be on-board the processor circuitry, in the same chip package as the processor circuitry and/or in one or more separate packages from the processor circuitry.

Figure 22:
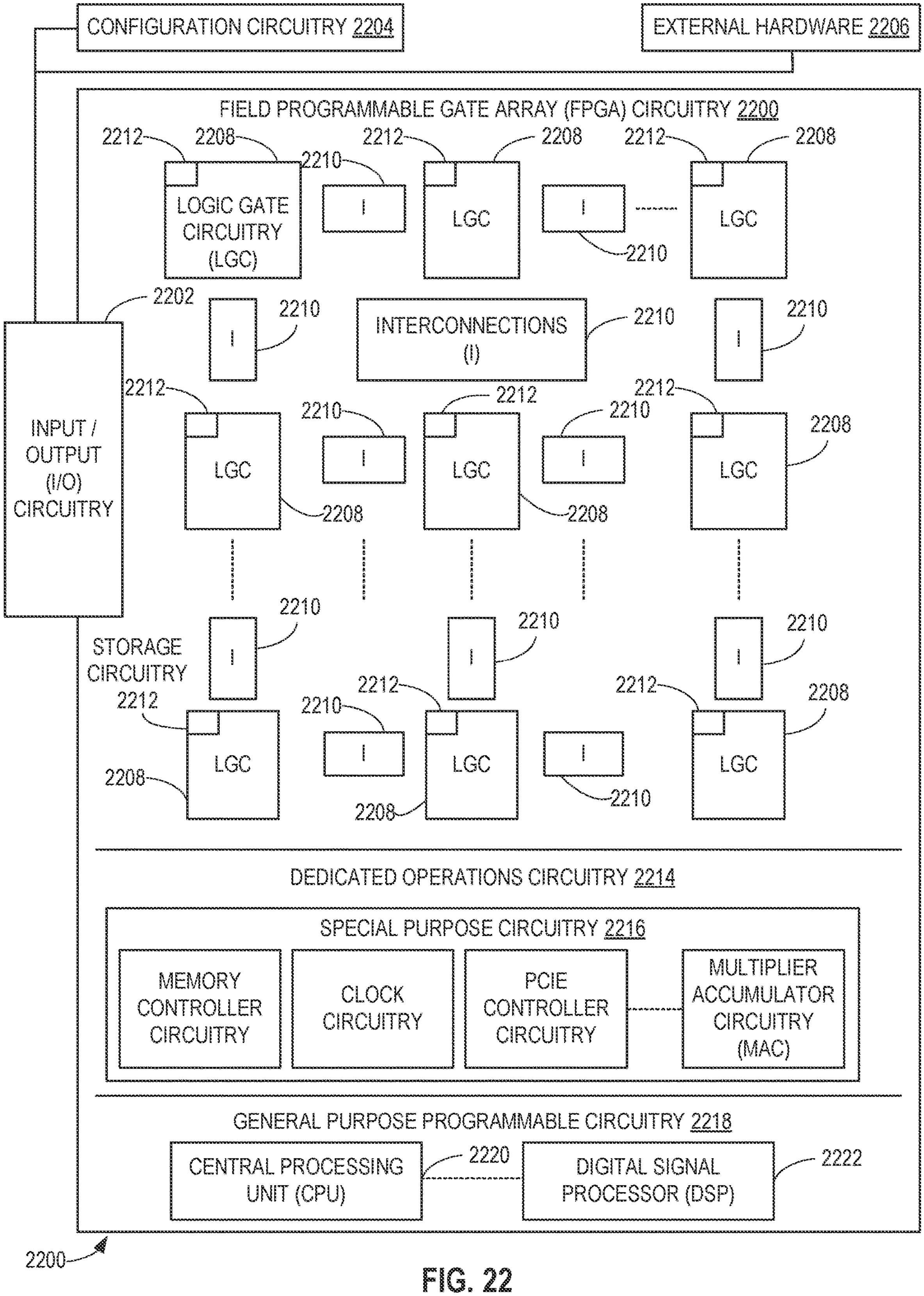
FIG. 22 is a block diagram of another example implementation of the processor circuitry of FIG. 20.

FIG. 22 is a block diagram of another example implementation of the processor circuitry 2012 of FIG. 20. In this example, the processor circuitry 2012 is implemented by FPGA circuitry 2200. For example, the FPGA circuitry 2100 may be implemented by an FPGA. The FPGA circuitry 2200 can be used, for example, to perform operations that could otherwise be performed by the example microprocessor 2100 of FIG. 21 executing corresponding machine readable instructions. However, once configured, the FPGA circuitry 2200 instantiates the machine readable instructions in hardware and, thus, can often execute the operations faster than they could be performed by a general purpose microprocessor executing the corresponding software.

More specifically, in contrast to the microprocessor 2100 of FIG. 21 described above (which is a general purpose device that may be programmed to execute some or all of the machine readable instructions represented by the flowcharts of FIGS. 17-19 but whose interconnections and logic circuitry are fixed once fabricated), the FPGA circuitry 2200 of the example of FIG. 22 includes interconnections and logic circuitry that may be configured and/or interconnected in different ways after fabrication to instantiate, for example, some or all of the machine readable instructions represented by the flowcharts of FIG. 17-19. In particular, the FPGA circuitry 2200 may be thought of as an array of logic gates, interconnections, and switches. The switches can be programmed to change how the logic gates are interconnected by the interconnections, effectively forming one or more dedicated logic circuits (unless and until the FPGA circuitry 2200 is reprogrammed). The configured logic circuits enable the logic gates to cooperate in different ways to perform different operations on data received by input circuitry. Those operations may correspond to some or all of the software represented by the flowcharts of FIGS. 17-19. As such, the FPGA circuitry 2200 may be structured to effectively instantiate some or all of the machine readable instructions of the flowcharts of FIG. 17-19 as dedicated logic circuits to perform the operations corresponding to those software instructions in a dedicated manner analogous to an ASIC. Therefore, the FPGA circuitry 2200 may perform the operations corresponding to the some or all of the machine readable instructions of FIGS. 17-19 faster than the general purpose microprocessor can execute the same.

In the example of FIG. 22, the FPGA circuitry 2200 is structured to be programmed (and/or reprogrammed one or more times) by an end user by a hardware description language (HDL) such as Verilog. The FPGA circuitry 2200 of FIG. 22, includes example input/output (I/O) circuitry 2202 to obtain and/or output data to/from example configuration circuitry 2204 and/or external hardware 2206. For example, the configuration circuitry 2204 may be implemented by interface circuitry that may obtain machine readable instructions to configure the FPGA circuitry 2200, or portion(s) thereof. In some such examples, the configuration circuitry 2204 may obtain the machine readable instructions from a user, a machine (e.g., hardware circuitry (e.g., programmed or dedicated circuitry) that may implement an Artificial Intelligence/Machine Learning (AI/ML) model to generate the instructions), etc. In some examples, the external hardware 2206 may be implemented by external hardware circuitry. For example, the external hardware 2206 may be implemented by the microprocessor 2100 of FIG. 21. The FPGA circuitry 2200 also includes an array of example logic gate circuitry 2208, a plurality of example configurable interconnections 2210, and example storage circuitry 2212. The logic gate circuitry 2208 and the configurable interconnections 2210 are configurable to instantiate one or more operations that may correspond to at least some of the machine readable instructions of FIGS. 17-19 and/or other desired operations. The logic gate circuitry 2208 shown in FIG. 22 is fabricated in groups or blocks. Each block includes semiconductor-based electrical structures that may be configured into logic circuits. In some examples, the electrical structures include logic gates (e.g., And gates, Or gates, Nor gates, etc.) that provide basic building blocks for logic circuits. Electrically controllable switches (e.g., transistors) are present within each of the logic gate circuitry 2208 to enable configuration of the electrical structures and/or the logic gates to form circuits to perform desired operations. The logic gate circuitry 2208 may include other electrical structures such as look-up tables (LUTs), registers (e.g., flip-flops or latches), multiplexers, etc.

The configurable interconnections 2210 of the illustrated example are conductive pathways, traces, vias, or the like that may include electrically controllable switches (e.g., transistors) whose state can be changed by programming (e.g., using an HDL instruction language) to activate or deactivate one or more connections between one or more of the logic gate circuitry 2208 to program desired logic circuits.

The storage circuitry 2212 of the illustrated example is structured to store result(s) of the one or more of the operations performed by corresponding logic gates. The storage circuitry 2212 may be implemented by registers or the like. In the illustrated example, the storage circuitry 2212 is distributed amongst the logic gate circuitry 2208 to facilitate access and increase execution speed.

The example FPGA circuitry 2200 of FIG. 22 also includes example Dedicated Operations Circuitry 2214. In this example, the Dedicated Operations Circuitry 2214 includes special purpose circuitry 2216 that may be invoked to implement commonly used functions to avoid the need to program those functions in the field. Examples of such special purpose circuitry 2216 include memory (e.g., DRAM) controller circuitry, PCIe controller circuitry, clock circuitry, transceiver circuitry, memory, and multiplier-accumulator circuitry. Other types of special purpose circuitry may be present. In some examples, the FPGA circuitry 2200 may also include example general purpose programmable circuitry 2218 such as an example CPU 2220 and/or an example DSP 2222. Other general purpose programmable circuitry 2218 may additionally or alternatively be present such as a GPU, an XPU, etc., that can be programmed to perform other operations.

Although FIGS. 21 and 22 illustrate two example implementations of the processor circuitry 2012 of FIG. 20, many other approaches are contemplated. For example, as mentioned above, modern FPGA circuitry may include an on-board CPU, such as one or more of the example CPU 2220 of FIG. 22. Therefore, the processor circuitry 2012 of FIG. 20 may additionally be implemented by combining the example microprocessor 2100 of FIG. 21 and the example FPGA circuitry 2200 of FIG. 22. In some such hybrid examples, a first portion of the machine readable instructions represented by the flowcharts of FIGS. 17-19 may be executed by one or more of the cores 2102 of FIG. 21, a second portion of the machine readable instructions represented by the flowcharts of FIGS. 17-19 may be executed by the FPGA circuitry 2200 of FIG. 22, and/or a third portion of the machine readable instructions represented by the flowcharts of FIGS. 17-19 may be executed by an ASIC. It should be understood that some or all of the circuitry of FIG. 2 may, thus, be instantiated at the same or different times. Some or all of the circuitry may be instantiated, for example, in one or more threads executing concurrently and/or in series. Moreover, in some examples, some or all of the circuitry of FIG. 2 may be implemented within one or more virtual machines and/or containers executing on the microprocessor.

In some examples, the processor circuitry 2012 of FIG. 20 may be in one or more packages. For example, the microprocessor 2100 of FIG. 21 and/or the FPGA circuitry 2200 of FIG. 22 may be in one or more packages. In some examples, an XPU may be implemented by the processor circuitry 2012 of FIG. 20, which may be in one or more packages. For example, the XPU may include a CPU in one package, a DSP in another package, a GPU in yet another package, and an FPGA in still yet another package.

Figure 23:
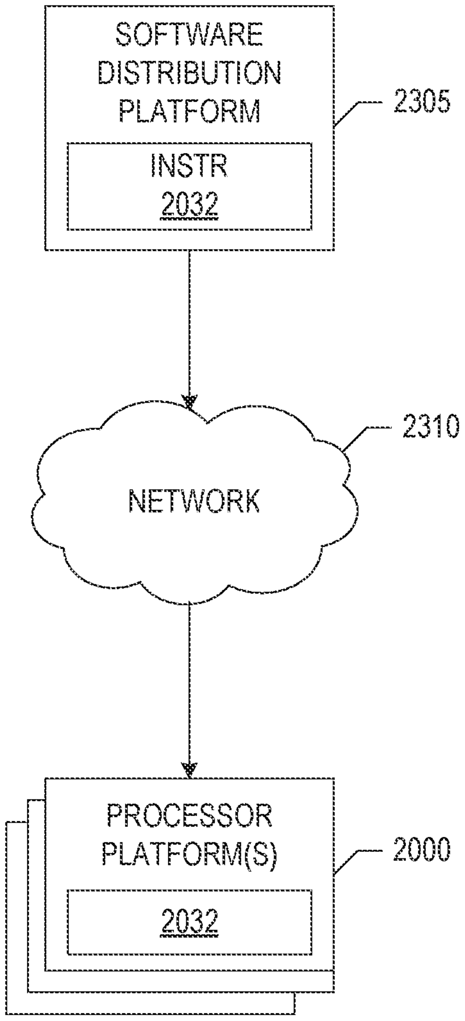
FIG. 23 is a block diagram of an example software distribution platform (e.g., one or more servers) to distribute software (e.g., software corresponding to the example machine readable instructions of FIGS. 17-19) to client devices associated with end users and/or consumers (e.g., for license, sale, and/or use), retailers (e.g., for sale, re-sale, license, and/or sub-license), and/or original equipment manufacturers (OEMs) (e.g., for inclusion in products to be distributed to, for example, retailers and/or to other end users such as direct buy customers).

A block diagram illustrating an example software distribution platform 2305 to distribute software such as the example machine readable instructions 2032 of FIG. 20 to hardware devices owned and/or operated by third parties is illustrated in FIG. 23. The example software distribution platform 2305 may be implemented by any computer server, data facility, cloud service, etc., capable of storing and transmitting software to other computing devices. The third parties may be customers of the entity owning and/or operating the software distribution platform 2305. For example, the entity that owns and/or operates the software distribution platform 2305 may be a developer, a seller, and/or a licensor of software such as the example machine readable instructions 2032 of FIG. 20. The third parties may be consumers, users, retailers, OEMs, etc., who purchase and/or license the software for use and/or re-sale and/or sub-licensing. In the illustrated example, the software distribution platform 2305 includes one or more servers and one or more storage devices. The storage devices store the machine readable instructions 2032, which may correspond to the example machine readable instructions 1700, 1702, 1710 of FIGS. 17-19, as described above. The one or more servers of the example software distribution platform 2305 are in communication with an example network 2310, which may correspond to any one or more of the Internet and/or any of the example networks 2026 described above. In some examples, the one or more servers are responsive to requests to transmit the software to a requesting party as part of a commercial transaction. Payment for the delivery, sale, and/or license of the software may be handled by the one or more servers of the software distribution platform and/or by a third party payment entity. The servers enable purchasers and/or licensors to download the machine readable instructions 2032 from the software distribution platform 2305. For example, the software, which may correspond to the example machine readable instructions 1700, 1702, 1710 of FIGS. 17-19, may be downloaded to the example processor platform 400, which is to execute the machine readable instructions 2032 to implement the heart rate detection circuitry 114. In some examples, one or more servers of the software distribution platform 2305 periodically offer, transmit, and/or force updates to the software (e.g., the example machine readable instructions 2032 of FIG. 20) to ensure improvements, patches, updates, etc., are distributed and applied to the software at the end user devices.

From the foregoing, it will be appreciated that example systems, methods, apparatus, and articles of manufacture have been disclosed that provide for measuring heart rate using a heterogeneous sensing system including a high resolution sensor such as a mmWave radar and a sensor having a lower resolution than the high resolution sensor, such as a camera. Examples disclosed herein remove artifacts associated with torso movement and respiratory harmonics that could otherwise interfere with detection of the heartbeat of the subject. Examples disclosed herein provide for contactless measurement of heart rate while providing for harmonics cancellation based on resolution differences between the sensors.

Example systems, apparatus, and methods for measuring heart rate are disclosed herein. Further examples and combinations thereof include the following:

Example 1 includes a system comprising a transmitter to emit electromagnetic waves; a first sensor to output signals representative of the electromagnetic waves reflected by a subject; a second sensor to generate image data, the image data including data corresponding to a chest of the subject; machine readable instructions; and processor circuitry to at least one of instantiate or execute the machine readable instructions to generate heartbeat data by cancelling harmonics associated with respiration by the subject from data corresponding to the output signals of the first sensor based on the image data; and determine a heart rate for the subject based on the heartbeat data.

Example 2 includes the system of example 1, wherein the image data including video frames and the processor circuitry is to identify coordinates of a pixel in a first one of the video frames, the pixel representing a portion of the chest of the subject; identify changes in the coordinates of the pixel in subsequent ones of the video frames; and generate a pixel value signal based on the coordinates of the pixel in the first one of the video frames and in the subsequent ones of the video frames.

Example 3 includes the system of examples 1 or 2, wherein the processor circuitry is to generate a first Short Time Fourier Transform spectrum based on the pixel value signal; generate a second Short Time Fourier Transform spectrum based on the data corresponding to the output signals of the first sensor; and subtract the first Short Time Fourier Transform spectrum from the second Short Time Fourier Transform spectrum to generate the heartbeat data.

Example 4 includes the system of any of examples 1-3, wherein the processor circuitry is to remove direct current (DC) components from the signals output by the first sensor to generate DC-filtered signals; and generate the second Short Time Fourier Transform spectrum based on data corresponding to the DC-filtered signals.

Example 5 includes the system of any of examples 1-4, wherein the first sensor includes a mmWave sensor.

Example 6 includes the system of any of examples 1-5, wherein the processor circuitry is to perform clustering of the heartbeat data to generate clustered heartbeat data; and determine the heart rate based on a cluster in the clustered heartbeat data.

Example 7 includes the system of any of examples 1-6, wherein the processor circuitry is to divide an environment in which the subject is located into a plurality of range bins; and detect a presence of the subject in a first one of the range bins based on the output signals of the first sensor, the data corresponding to the output signals of the first sensor based on the signals associated with the first one of the range bins.

Example 8 includes the system of any of examples 1-7, wherein the processor circuitry is to detect the presence of the subject in the first one of the range bins based on the output signals of the first sensor and coordinates of a pixel representative of a portion of the chest of the subject in the image data.

Example 9 includes the system of any of examples 1-8, wherein the transmitter and the first sensor are part of a transceiver.

Example 10 includes a non-transitory machine readable storage medium comprising instructions to cause processor circuitry to at least generate a pixel value signal representing changes in coordinates of at least one pixel in video frames over time, the at least one pixel corresponding to a chest of a subject in image data, the image data generated by a camera; and generate heartbeat data for the subject based on (a) signal data corresponding to signals output by a sensor, the sensor having a higher resolution than the camera, and (b) the pixel value signal.

Example 11 includes the non-transitory machine readable storage medium of example 10, wherein the instructions cause the processor circuitry to subtract the pixel value signal from the signal data to generate the heartbeat data.

Example 12 includes the non-transitory machine readable storage medium of examples 10 or 11, wherein the instructions cause the processor circuitry to generate a first Short Time Fourier Transform spectrum based on the pixel value signal; generate a second Short Time Fourier Transform spectrum based on the signal data; and subtract the first Short Time Fourier Transform spectrum from the second Short Time Fourier Transform spectrum to generate the heartbeat data.

Example 13 includes the non-transitory machine readable storage medium of any of examples 10-12, wherein the instructions cause the processor circuitry to cluster the heartbeat data to generate clustered heartbeat signal data; and identify a heart rate based on the clustered heartbeat signal data.

Example 14 includes the non-transitory machine readable storage medium of any of examples 10-13, wherein the instructions, when executed, cause the processor circuitry to identify the heart rate based on an average of the clustered heartbeat data.

Example 15 includes the non-transitory machine readable storage medium of any of examples 10-14, wherein the instructions cause the processor circuitry to normalize the pixel value signal and the signal data; and generate the heartbeat data based on the normalized pixel value signal and the normalized signal data.

Example 16 includes the non-transitory machine readable storage medium of any of examples 10-15, wherein the instructions cause the processor circuitry to define a plurality of range bins in an environment in which the subject is located; and detect a presence of the subject in a first one of the range bins based on the signals output by the sensor, the signal data corresponding to the signals associated the first one of the range bins.

Example 17 includes an apparatus comprising means for detecting reflected radar signals, the reflected radar signals indicative of displacement of a chest of a subject; means for generating image data, the image data corresponding to displacement of the chest of the subject over time; means for detecting a chest point in the image data, the chest point detecting means to identify a portion of the chest in the image data; means for tracking the portion of the chest in the image data, the tracking means to generate a value signal based on the tracking of the portion of the chest in the image data; and means for cancelling harmonics, the harmonics cancelling means to remove respiratory harmonics from data corresponding to the reflected radar signals based on the value signal to generate heartbeat data.

Example 18 includes the apparatus of example 17, further including means for clustering, the clustering means to cluster the heartbeat data; and means for measuring heart rate based on the clustered heartbeat data.

Example 19 includes the apparatus of examples 17 or 18, further including means for removing direct current artifacts from the reflected radar signals.

Example 20 includes the apparatus of any of examples 17-19, wherein the harmonics cancelling means is to subtract the value signal from the data corresponding to the reflected radar signals.

Example 21 includes the apparatus of any of examples 17-20, further including means for signal transforming, the signal transforming means to generate Short Time Fourier Transform spectrums for the data corresponding to the reflected radar signals and the value signal, respectively, the harmonics cancelling means to subtract the Short Time Fourier Transform spectrum for the value signal from the Short Time Fourier Transform spectrum for the data corresponding to the reflected radar signals.

The following claims are hereby incorporated into this Detailed Description by this reference. Although certain example systems, methods, apparatus, and articles of manufacture have been disclosed herein, the scope of coverage of this patent is not limited thereto. On the contrary, this patent covers all systems, methods, apparatus, and articles of manufacture fairly falling within the scope of the claims of this patent.

What is claimed is:

1. A system comprising:

a transmitter to emit electromagnetic waves;

a first sensor to output signals representative of the electromagnetic waves reflected by a subject in an environment, the first sensor having a first resolution;

a second sensor to generate image data, the image data including data corresponding to a chest of the subject, the second sensor having a second resolution lower than the first resolution;

machine-readable instructions; and at least one processor circuit to at least one of instantiate or execute the machine-readable instructions to:

identify range bins indicative of a presence of objects in the environment based on the signals output by the first sensor, the objects including the subject;

generate phase signals for the range bins, the phase signals corresponding to the signals output by the first sensor, the phase signals including a first phase signal associated with a first range bin of the range bins;

generate a pixel value signal based on coordinates of a pixel in first data of the image data and coordinates of the pixel in second data of the image data, the pixel representing a portion of the chest of the subject;

select the first range bin based on a correlation between the first phase signal and the pixel value signal;

generate heartbeat data by cancelling harmonics associated with respiration by the subject from the first phase signal based on the pixel value signal; and determine a heart rate for the subject based on the heartbeat data.

2. The system of claim 1, wherein the image data including video frames and one or more of the at least one processor circuit is to:

identify coordinates of the pixel in a first one of the video frames;

identify changes in the coordinates of the pixel in subsequent ones of the video frames, the subsequent ones of the video frames corresponding to the second data of the image data; and generate the pixel value signal based on the coordinates of the pixel in the first one of the video frames and in the subsequent ones of the video frames.

3. The system of claim 2, wherein one or more of the at least one processor circuit is to:

generate a first Short Time Fourier Transform spectrum based on the pixel value signal;

generate a second Short Time Fourier Transform spectrum based on the first sensor first phase signal; and subtract the first Short Time Fourier Transform spectrum from the second Short Time Fourier Transform spectrum to generate the heartbeat data.

4. The system of claim 3, wherein one or more of the at least one processor circuit is to:

remove direct current (DC) components from the phase signals to generate DC-filtered signals; and generate the second Short Time Fourier Transform spectrum based on data corresponding to the DC-filtered signals.

5. The system of claim 1, wherein the first sensor includes a mmWave sensor.

6. The system of claim 1, wherein one or more of the at least one processor circuit is to:

perform clustering of the heartbeat data to generate clustered heartbeat data; and determine the heart rate based on a cluster in the clustered heartbeat data.

7. The system of claim 1, wherein one or more of the at least one processor circuit is to:

divide the environment into a plurality of range bins; and detect a presence of the subject in the first range bin based on phase properties of the first phase signal.

8. The system of claim 7, wherein one or more of the at least one processor circuit is to detect the presence of the subject in the first range bin based on the phase signal associated with the first range bin having a modulated phase.

9. A non-transitory machine-readable storage medium comprising machine-readable instructions to cause at least one processor circuit to at least:

generate a pixel value signal representing changes in coordinates of at least one pixel in video frames over time, the at least one pixel corresponding to a chest of a subject in image data, the image data generated by a camera;

generate phase signals corresponding to range bins indicative of a presence of objects in an environment based on signals output by a sensor, the sensor having a higher resolution than the camera, the objects including the subject, the phase signals including a first phase signal associated with a first range bin of the range bins;

select the first range bin based on a correlation between the first phase signal and the pixel value signal; and generate heartbeat data by cancelling harmonics associated with respiration by the subject from the first phase signal based on the pixel value signal.

10. The non-transitory machine-readable storage medium of claim 9, wherein the machine-readable instructions are to cause one or more of the at least one processor circuit to subtract the pixel value signal from the first phase signal to generate the heartbeat data.

11. The non-transitory machine-readable storage medium of claim 10, wherein the machine-readable instructions are to cause one or more of the at least one processor circuit to:

generate a first Short Time Fourier Transform spectrum based on the pixel value signal;

generate a second Short Time Fourier Transform spectrum based on the first phase signal associated with the first range bin; and subtract the first Short Time Fourier Transform spectrum from the second Short Time Fourier Transform spectrum to generate the heartbeat data.

12. The non-transitory machine-readable storage medium of claim 9, wherein the machine-readable instructions are to cause one or more of the at least one processor circuit to:

cluster the heartbeat data to generate clustered heartbeat signal data; and identify a heart rate based on the clustered heartbeat signal data.

13. The non-transitory machine-readable storage medium of claim 12, wherein the machine-readable instructions are to cause one or more of the at least one processor circuit to identify the heart rate based on an average of the clustered heartbeat data.

14. The non-transitory machine-readable storage medium of claim 9, wherein the machine-readable instructions are to cause one or more of the at least one processor circuit to:

normalize the pixel value signal and the first phase signal; and generate the heartbeat data based on the normalized pixel value signal and the normalized first phase signal-data.

15. The non-transitory machine-readable storage medium of claim 9, wherein the machine-readable instructions are to cause one or more of the at least one processor circuit to:

define a plurality of range bins in the environment; and detect a presence of the subject in the first range bin based on the signals output by the sensor.

16. An apparatus comprising:

means for detecting reflected radar signals, the reflected radar signals indicative of displacement of a chest of a subject;

means for generating image data, the image data corresponding to displacement of the chest of the subject over time;

means for detecting a chest point in the image data, the means for detecting to identify a portion of the chest in the image data;

means for tracking the portion of the chest in the image data, the means for tracking to generate a pixel value signal based on the tracking of the portion of the chest in the image data;

means for phase unwrapping to generate phase signals corresponding to range bins indicative of a presence of objects in an environment based on the reflected radar signals, the objects including the subject, the phase signals including a first phase signal associated with a first range bin of the range bins;

means for range bin selecting, the means for range bin selecting to select the first range bin based on a correlation between the first phase signal and the pixel value signal; and means for cancelling harmonics, the means for cancelling harmonics to remove respiratory harmonics from first phase signal based on the pixel value signal to generate heartbeat data.

17. The apparatus of claim 16, further including:

means for clustering, the means for clustering to cluster the heartbeat data; and means for measuring heart rate based on the clustered heartbeat data.

18. The apparatus of claim 16, further including means for removing direct current artifacts from the phase signals.

19. The apparatus of claim 16, wherein the means for cancelling harmonics is to subtract the pixel value signal from the first phase signal.

20. The apparatus of claim 19, further including means for signal transforming, the means for signal transforming to generate Short Time Fourier Transform spectrums for the first phase signal and the pixel value signal, respectively, the means for cancelling harmonics to subtract the Short Time Fourier Transform spectrum for the pixel value signal from the Short Time Fourier Transform spectrum for the first phase signal.

* * * * *